United States Patent
Grader et al.

(10) Patent No.: US 9,746,431 B2
(45) Date of Patent: Aug. 29, 2017

(54) METHOD AND SYSTEM FOR MULTI-ENERGY COMPUTER TOMOGRAPHIC CUTTINGS ANALYSIS

(71) Applicant: Ingrain, Inc., Houston, TX (US)

(72) Inventors: Avrami Grader, Houston, TX (US); Naum Derzhi, Houston, TX (US); Bryan Guzman, Houston, TX (US)

(73) Assignee: Ingrain, Inc., Houston, TX (US)

( * ) Notice: Subject to any disclaimer, the term of this patent is extended or adjusted under 35 U.S.C. 154(b) by 804 days.

(21) Appl. No.: 13/890,367

(22) Filed: May 9, 2013

(65) Prior Publication Data
US 2013/0301794 A1 Nov. 14, 2013

Related U.S. Application Data

(60) Provisional application No. 61/652,567, filed on May 29, 2012, provisional application No. 61/646,045, filed on May 11, 2012.

(51) Int. Cl.
*G01N 23/04* (2006.01)
*G01N 23/087* (2006.01)
(Continued)

(52) U.S. Cl.
CPC ......... *G01N 23/046* (2013.01); *G01N 23/087* (2013.01); *G01N 1/36* (2013.01);
(Continued)

(58) Field of Classification Search
CPC .... G01N 23/046; G01N 23/087; G01N 23/10; G01N 2223/045; G01N 2223/302;
(Continued)

(56) References Cited

U.S. PATENT DOCUMENTS

| 4,542,648 A * | 9/1985 | Vinegar | E21B 49/00 73/152.07 |
| 4,571,491 A * | 2/1986 | Vinegar | G01N 23/083 250/252.1 |

(Continued)

OTHER PUBLICATIONS

International Search Report and Written Opinion issued in corresponding International Patent Application No. PCT/US2013/040259 dated Aug. 22, 2013 (12 pages).

(Continued)

*Primary Examiner* — Thomas R Artman
(74) *Attorney, Agent, or Firm* — Kilyk & Bowersox, P.L.L.C.

(57) ABSTRACT

A method and a system are provided to prepare a plurality of cuttings or other rock fragments or other porous media, such as cuttings from a drilling interval or multiple intervals, for computer tomographic scanning at the same time. A method and system also are provided to allow organization of mass quantities of cuttings or other rock fragments obtained from intervals of a well to more accurately categorize the cuttings to assist selections thereof for more detailed digital rock analysis, such as using SEM and FIB-SEM systems, are provided. A method and system also are provided to allow characterization of facies occurrence frequency of a depth interval using drill cuttings or other rock fragments. Computerized systems, computer readable media, and programs for performing the methods are also provided.

4 Claims, 15 Drawing Sheets

(51) Int. Cl.
*G01N 23/10* (2006.01)
*G01N 1/36* (2006.01)
(52) U.S. Cl.
CPC ....... *G01N 23/10* (2013.01); *G01N 2223/419* (2013.01); *G01N 2223/616* (2013.01); *G01N 2223/649* (2013.01)
(58) Field of Classification Search
CPC ..... G01N 2223/303; G01N 2223/3037; G01N 2223/423; G01N 2223/426; G01N 2223/601; G01N 2223/616; G01N 2223/639
See application file for complete search history.

(56) References Cited

U.S. PATENT DOCUMENTS

| | | | |
|---|---|---|---|
| 4,856,341 A | 8/1989 | Vinegar et al. | |
| 4,884,455 A | 12/1989 | Vinegar et al. | |
| 5,063,509 A * | 11/1991 | Coles ................. | G01N 23/046 250/269.1 |
| 5,164,590 A * | 11/1992 | Coles ................. | G01N 23/046 250/253 |
| 6,393,906 B1 * | 5/2002 | Vityk ................. | G01N 33/241 166/269 |
| 6,516,080 B1 | 2/2003 | Nur | |
| 6,876,721 B2 * | 4/2005 | Siddiqui ............ | G01N 23/046 250/269.3 |
| 8,081,796 B2 * | 12/2011 | Derzhi ............... | E21B 49/005 378/53 |
| 8,081,802 B2 * | 12/2011 | Dvorkin ............ | G01N 23/046 175/249 |
| 8,085,974 B2 * | 12/2011 | Dvorkin ............ | G06T 7/0004 378/21 |
| 8,155,377 B2 * | 4/2012 | Dvorkin ............ | E21B 47/00 175/249 |
| 8,170,799 B2 * | 5/2012 | Dvorkin ............ | G01V 1/30 702/11 |
| 8,331,626 B2 * | 12/2012 | Wojcik .............. | G01N 23/046 382/109 |
| 8,583,410 B2 * | 11/2013 | Sisk .................. | G01N 33/24 702/6 |
| 8,590,382 B2 * | 11/2013 | Zaleski, Jr. ........ | E21B 43/119 166/250.01 |
| 8,716,673 B2 * | 5/2014 | Routh, Jr. .......... | H01J 27/16 250/306 |
| 8,855,264 B2 * | 10/2014 | Derzhi ............... | G01N 23/087 378/5 |
| 8,938,045 B2 * | 1/2015 | Dvorkin ............ | G01N 23/046 250/253 |
| 9,064,328 B2 * | 6/2015 | Carpio ............... | G06T 5/50 |
| 9,127,529 B2 * | 9/2015 | Guzman ............ | E21B 49/02 |
| 9,201,026 B2 * | 12/2015 | Walls ................. | G01N 23/22 |
| 9,275,828 B2 * | 3/2016 | Routh, Jr. .......... | H01J 27/16 |
| 2009/0288880 A1 | 11/2009 | Wojcik et al. | |
| 2010/0131204 A1 * | 5/2010 | Dvorkin ............ | G06T 7/0004 702/6 |
| 2011/0181701 A1 * | 7/2011 | Varslot .............. | G06T 7/0024 348/46 |
| 2013/0028371 A1 * | 1/2013 | Derzhi ............... | G01N 23/087 378/5 |
| 2013/0073207 A1 * | 3/2013 | Ganz ................. | G01N 33/24 702/8 |
| 2013/0094716 A1 * | 4/2013 | Carpio ............... | G06T 5/50 382/109 |
| 2013/0134307 A1 * | 5/2013 | Routh, Jr. .......... | H01J 27/16 250/305 |
| 2013/0182819 A1 * | 7/2013 | Dvorkin ............ | G01N 23/046 378/5 |
| 2013/0259190 A1 * | 10/2013 | Walls ................. | G01N 23/22 378/9 |
| 2013/0301794 A1 * | 11/2013 | Grader .............. | G01N 23/046 378/5 |
| 2013/0306765 A1 | 11/2013 | Tavakkoli et al. | |
| 2014/0117231 A1 * | 5/2014 | Owen ................ | H01J 37/28 250/307 |
| 2014/0119497 A1 * | 5/2014 | Guzman ............ | E21B 49/02 378/5 |
| 2014/0326877 A1 * | 11/2014 | Routh, Jr. .......... | H01J 27/16 250/307 |
| 2014/0361466 A1 * | 12/2014 | Kimour ............. | G01N 1/36 264/496 |

OTHER PUBLICATIONS

Rosenberg, E., et al., "Microtomography applications in rock analysis and related fields," Computerized Tomography for Industrial Applications and Image Processing in Radiology, Mar. 15-17, 1999, Berlin, Germany, DGZfP-Proceedings BB 67-CD, Paper 2, pp. 9-18.

Freifeld, B. et al., "On-Site Geologic Core Analysis Using a Portable X-ray Computed Tomographic System," Lawrence Berkeley National Laboratory, Mar. 1, 2004, (25 pages).

Coles, M. E., et al., "Applications of Cat Scanning for Oil and Gas Production Research," Mobil Research and Development Corporation, IEEE, 1990, pp. 804-809.

Sisk, C., et al., "3D Visualization and Classification of Pore Structure and Pore Filling in Gas Shales," Society of Petroleum Engineers Annual Techn. Conf. & Exhibit, Florence Italy, SPE 134582, Sep. 2010, pp. 1-4.

Curtis, M. E., et al., "Structural Characterization of Gas Shales on the Micro- and Nano-Scales," Canadian Unconventional Resources & Int'l Petroleum Conf., Calgary, Alberta, Canada, CUSG/SPE 137693, Oct. 2010, pp. 1-15.

Office Action and Search Report issued in corresponding Chinese Patent Application No. 201380036962.6 dated May 26, 2016 (with English translation) (16 pages).

* cited by examiner

Density Map Legend a ▨ Between 2.5 and 2.6 g/cc b ▨ Greater than 2.6 g/cc c ▨ Between 2.4 and 2.45 g/cc d ▨ Between 2.45 and 2.5 g/cc Zeff Map Legend 1 ▨ Between Quartz and Calcite Line 2 ▨ Greater than Calcite Line 3 ▨ Lower than Quartz Line

| Porosity and Materials* (%) | |
|---|---|
| Total Porosity | 8.3 |
| Porosity associated with Kerogen | 3.1 |
| Total Organic Content | 6.3 |
| Connected Porosity* (%) | |
| X-Axis | 4.6 |
| Y-Axis | 4.6 |
| Z-Axis | 4.6 |
| Permeability (nD) | |
| X-Axis | 46 |
| Y-Axis | 12 |
| Z-Axis | 95 |

FIG. 15

METHOD AND SYSTEM FOR MULTI-ENERGY COMPUTER TOMOGRAPHIC CUTTINGS ANALYSIS

This application claims the benefit under 35 U.S.C. §119 (e) of prior U.S. Provisional Patent Application Nos. 61/646,045, filed May 11, 2012, and 61/652,567, filed May 29, 2012, which are incorporated in their entireties by reference herein.

BACKGROUND OF THE INVENTION

This invention relates to the field of digital rock physics and, more particularly, to methods to select drill cuttings or other rock fragments for further analysis and to characterize facies occurrence frequency of a depth interval using drill cuttings or other rock fragments.

Estimating rock properties, such as porosity, total organic content, permeability, and composition, and so forth, has substantial significance, such as for characterizing the economic value of reservoir rock formations. Laboratory analysis of rock samples can be difficult and time consuming. Physical lab experiments are difficult to perform due to the size and shape of cuttings. Devices for generating digital images of rock samples have become available. These devices include, for example, computer tomographic (CT) devices, scanning electron microscopy (SEM) devices, and FIB-SEM (focused ion beam combined with SEM) devices.

Along with technological advances to help analyze geologic features, advances in workflow have been created. For example, a workflow has been shown which has three basic steps of (a) 3D CT imaging and/or FIB-SEM (focused ion beam combined with SEM) imaging; (b) segmentation of the digital volume to quantitatively identify the components, including the mineral phases, organic-filled pores, and free-gas inclusions; and (c) computations of TOC (Total Organic Content), porosity, pore connectivity, and permeability in the three axis. Sisk et al, SPE 134582, "3D Visualization and Classification of Pore Structure and Pore Filling in Gas Shales", 2010. Using FIB-SEM technology, a sample is analyzed in three dimensions by creating a plurality of two-dimensional images. The segmentation process can be done by, assigning gray scale ranges to features, and volumes can be constructed which show three dimensional distributions of these features. Curtis et al, SPE 137693, "Structural Characterization of Gas Shales on the Micro- and nano-Scales", 2010. The features that are present within the rock can include, but are not limited to, pores, organic matter, and rock matrix.

Large samples of porous rock are required in order to obtain estimates of rock properties such as permeability, porosity, total organic content, elasticity and other properties that are typical of an entire subterranean rock formation or facies. One common sample used to estimate rock properties is a well core. Well cores are very small compared to an entire formation, so multiple well cores are typically taken and analyzed and rock properties are interpolated in between geographic locations of the cores. When rock properties are estimated using digital rock physics, the problem of sample size versus formation or facies size is even more extreme. Digital rock physics techniques for estimating rock properties have the advantage that they can accurately scan and produce digital images of very fine pore structures and they can identify small volumes of organic materials present in the pore structure of the rock. However, it is very time consuming and expensive to digitally scan very large samples to estimate rock properties. For example, shale rocks can have an average pore size of about 0.005 to 1.0 µm and a well core typically can be about 100,000 µm in diameter and 1,000,000 µm or more in length. The volume of such a core is about $8 \times 10^{15}$ µm$^3$ while the volume of a single pore in a shale rock is about $5 \times 10^{-4}$ µm$^3$, assuming spherical pores that are 0.1 µm in diameter. Thus the volume of the entire sample (core) is almost 20 orders of magnitude (i.e., $10^{20}$ times) greater than the volume of a typical pore. The difference in scale between the sample (core) and the pores contained in the sample can complicate pore analysis thereof. Scanning the entire sample at a resolution high enough to identify all of the pores can result in a complete assessment of the pore structure of the sample. However, scanning the entire sample at a resolution high enough to identify all of the pores is not practical due to the time and expense required to do a complete scan.

In addition, some underground formations such as shale rocks can have many very thin facies, sometimes only a few millimeters or centimeters thick. The accuracy of core depth estimates is on the order of 3 meters. Boreholes can be horizontally separated by hundreds or thousands meters on the surface. Each borehole provides a point of information about the underground formation at a specific surface location. The geologist must interpolate between borehole locations to estimate the location of a facies of interest in between borehole vocations. Underground facies typically do not follow straight lines and as such, significant errors in estimating location of facies can occur. Further, with the advent of horizontal drilling the need to have more detailed information about the precise location of facies and facie properties has become more important. It may not be practical to extract horizontal cores from a well bore and vertical cores may provide only limited data. Core analysis is not practical in real time or near-real time. Cores must be extracted and shipped to a laboratory for analysis and this can require many days or weeks to complete. As a result, core analysis can have reduced value to questions that arise at the time a well is being drilled. Therefore, reliance on cores to estimate properties of subterranean formations can have several shortcomings.

The present investigators have recognized that there is a need for reliable and accurate cuttings preparation, categorization, and sample selection features that can be integrated with methods of high resolution analysis of rock samples.

SUMMARY OF THE INVENTION

A feature of the present invention is a method and system that assists the preparation of a plurality of rock fragments, such as cuttings or other porous media samples, for computer tomographic scanning at the same time.

A further feature of the present invention is a method and system for categorizing rock fragments of one or more drilling intervals using multi-energy X-ray digital scanning and improved processing and analysis of the digital images generated thereby for selection of a rock fragment for further digital analysis.

Another feature of the present invention is a method and a system that assists selection of an optimal rock fragment from a larger group of rock fragments obtained from the same drilling interval for further detailed analysis.

A further feature of the present invention is a method and a system to allow organization of mass quantities of rock fragments obtained from multiple intervals of a well to more accurately categorize the rock fragments to assist selections thereof for more detailed digital rock analysis, such as using SEM and FIB-SEM systems.

A further feature of the present invention is a method and a system to select a rock fragment from a larger group of rock fragments obtained from the same interval upon which a further detailed analysis is performed to characterize the rock formation or rock facies at the interval from which the rock fragments were obtained.

Another feature of the present invention is a method for characterizing rock fragments of a drilling interval using multi-energy X-ray digital scanning and improved processing and analysis of the output generated thereby, wherein clusters (families) of individual rock fragments within a given depth interval can be identified which have similar density and atomic number, and data values resulting from analysis of individual rock fragments can be combined with rock fragment frequency distribution among clusters to provide a frequency distribution (histogram) of property values within the given depth interval.

A further feature of the present invention is repeating this analysis through all of the depth intervals of a well to provide a log that displays the frequency distribution of facies along the entire well.

Another further feature of the present invention is a system for implementing these methods and outputting the results, for example, displaying the results, printing the results, storing the results in a memory device, or streaming the results to a downstream processor so that they can be further utilized.

A further feature of the present invention is a method and system to estimate rock properties in a time frame which is short enough in duration to be able to use the estimated rock properties to make decisions during well drilling or completion.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a method for processing rock fragments for computer tomographic scanning, comprising positioning a plurality of rock fragments in space positions in a stabilizing material to provide a rock fragments-embedded carrier, and performing a multi-energy X-ray CT scan of the rock fragments-embedded carrier comprising the plurality of rock fragments with at least 3 reference objects.

The present invention further relates to a method for preparing rock fragments for computer tomographic scanning which comprises steps of (a) positioning a plurality of rock fragments, such as drill cuttings, in spaced positions in a casting container, (b) introducing flowable polymer into the casting container to encapsulate the rock fragments, (c) hardening the polymer to form a rock fragments-embedded carrier, and (d) removing the rock fragments-embedded carrier from the casting container.

The present invention further relates in part to a method for categorizing rock fragments within an X-ray digital scan for selection of a rock fragment for further digital analysis which comprises steps of (a) performing a multi-energy X-ray CT scan of a rock fragments-embedded carrier comprising a plurality of rock fragments with at least 3 reference objects, (b) creating digital images of the rock fragments from the multi-energy X-ray CT scan, wherein each of the rock fragments scanned at two or more different energy levels returns a CT value for each voxel thereof, (c) estimating bulk density, RhoB, and effective atomic number, $Z_{eff}$, for each of the rock fragments as data pairs based on the digital images of the rock fragments, comprising averaging the voxels for each entire rock fragment per different energy scan and processing the average values for each rock fragment to provide the data pairs, (d) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (a), and (e) selecting at least one rock fragment from the set or subsets as applicable for further digital analysis.

The present invention further relates in part to a method for organizing and categorizing rock fragments within an X-ray digital scan for selection of a rock fragment for further digital analysis, which comprises the indicated steps (a)-(d), wherein in step (a), the rock fragments comprise a first plurality of rock fragments which are obtained from a same first interval. The rock fragments-embedded carrier optionally can further comprise a second plurality of rock fragments obtained from a same second interval, wherein the first and second intervals are different. The multi-energy X-ray CT scan can further comprise scanning a second rock fragments-embedded carrier stacked with the first rock fragments-embedded carrier, wherein the second rock fragments-embedded carrier can comprise a second plurality of rock fragments obtained from a second interval which is different than the first interval, and the indicated steps (b), (c) and (d) can also done for the second rock fragments-embedded carrier.

The present invention further relates in part to a method for organizing and categorizing rock fragments within an X-ray digital scan for selection of a rock fragment for further digital analysis which comprises steps of (a) positioning a plurality of rock fragments in space positions in a stabilizing material to provide a rock fragments-embedded carrier, (b) performing a multi-energy X-ray CT scan of the rock fragments-embedded carrier comprising the rock fragments with at least 3 reference objects, (c) creating digital images of the rock fragments from the multi-energy X-ray CT scan, wherein each of the rock fragments scanned at two or more different energy levels returns a CT value for each voxel thereof, (d) estimating the bulk density, RhoB, and effective atomic number, $Z_{eff}$, for each of the rock fragments as data pairs based on the digital images of the rock fragments, comprising averaging the voxels for the entire rock fragment per different energy scan and processing the average values for each rock fragment to provide the data pairs, (e) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (e), and (f) selecting at least one rock fragment from the set or subsets as applicable for further digital analysis.

The present invention further relates in part to a method for organizing and categorizing rock fragments within an X-ray digital scan for selection of a rock fragment for further digital analysis which comprises steps of (a) positioning rock fragments of the same drilling interval in spaced positions in a casting container, (b) introducing flowable polymer into the casting container to encapsulate the rock fragments, (c) hardening the polymer to form a rock fragments-embedded carrier, (d) removing the rock fragments-embedded carrier from the casting container, (e) performing a multi-energy X-ray CT scan of the rock fragments-embedded carrier with at least 3 reference objects, (f) creating digital images of the rock fragments from the multi-energy X-ray CT scan, (g) estimating bulk density, RhoB, and effective atomic number, $Z_{eff}$, for each of the rock fragments as data pairs based on the digital images of the rock fragments as indicated, (h) categorizing the bulk density, RhoB, and effective atomic number, $Z_{eff}$, data pairs into a single set for a single rock fragments-embedded carrier, all carriers, or separate subsets if more than one rock fragments-embedded carrier of differing intervals is scanned in step (e), and (i) selecting at least one rock fragment from the set or subsets as applicable for further digital analysis.

The present invention further relates in part to a method for estimating selected physical properties of a rock sample, which comprises the indicated steps (a)-(i) and the additional steps of: (j) extracting the at least one selected rock fragment or other rock sample from the carrier, (k) creating 2D digital images of the selected rock fragment using an SEM, (l) estimating at least one of porosity, organic matter content, and mineralogy from the images created in step (k), (m) selecting a subarea of the images created in step (k), which can comprise at least one of relatively high porosity and high organic matter or other features of interest, (n) imaging the selected subarea of step (m) with a FIB-SEM, (o) creating 3D digital images from the imaging in step (n), (p) segmenting the 3D digital images of step (o) to identify voxels as pore, rock or organic matter, and (q) estimating rock properties from the segmented images.

The present invention further relates in part to a method for characterizing facies occurrence frequency of a depth interval using rock fragments, comprising steps (a)-(e) described below. In step (a), a multi-energy X-ray CT scan of a plurality of rock fragments of a depth interval with at least 3 reference objects at two or more different energy levels is performed. In step (b), digital images of the rock fragments are created from the multi-energy X-ray CT scan, wherein each of the rock fragments scanned at two or more different energy levels returns a CT value for each voxel thereof and for each energy level. In step (c) bulk density, RhoB, and effective atomic number, $Z_{eff}$, for each of the rock fragments are estimated as data pairs based on the digital images of the rock fragments, which comprises averaging the voxels for each entire rock fragment per different energy scan and processing the average values for each rock fragment to provide the data pairs. In step (d), the bulk density, RhoB, and effective atomic number, $Z_{eff}$, data pairs are categorized and clusters are identified, wherein the clusters identify different respective facies of rock of the depth interval. In step (e), an occurrence frequency distribution of the rock fragments with respect to the clusters is determined based on (i) the number of rock fragments in each cluster, and (ii) the total number of rock fragments. The occurrence frequency distribution of the rock fragments correlates with occurrence frequency distribution of the identified facies in the depth interval.

The present invention further relates to a method for determining a bulk property of a depth interval of a rock formation, comprising steps (a)-(g) described below. In step (a), a sample of a depth interval of a rock formation is obtained, wherein the sample comprises a plurality of rock fragments. In step (b), the plurality of rock fragments from the depth interval and at least three reference objects are imaged using dual energy X-ray CT scanning. In step (c), bulk density, RhoB, and effective atomic number, $Z_{eff}$, for each of the rock fragments are estimated as data pairs based on the digital images of the rock fragments, which comprises averaging the voxels for each entire rock fragment per different energy scan and processing the average values for each rock fragment to provide the data pairs. In step (d), the bulk density, RhoB, and effective atomic number, $Z_{eff}$, data pairs are categorized and clusters are identified, wherein the clusters identify different respective facies of rock of the depth interval. In step (e), a physical or chemical property of at least one rock fragment of each of the different facies is determined, wherein the physical or chemical property determined is the same for each rock fragment of the different facies of the at least one rock fragment. In step (f), the frequency distribution of each of the different facies is calculated based on (i) the total number of rock fragments in the plurality of rock fragments, and (ii) the total number of rock fragments of each of the different facies of the plurality of different facies. In step (g), a bulk property of the depth interval is determined based on (i) the determined physical or chemical property of the rock fragments of the different facies, and (ii) the frequency distribution of each of the different facies.

The present invention further relates in part to a system for organizing and categorizing rock fragments within an X-ray digital scan for selection of a rock fragment for further analysis, comprising (a) a preparation station comprising a plurality of rock fragments of the same drilling interval positioned in spaced apart locations in a casting container, wherein the rock fragments are embedded in a hardened polymer to provide a rock fragments-embedded carrier, (b) a multi-energy X-ray CT scanner having a stage capable of holding one or more rock fragments-embedded carriers in stacked arrangement and a plurality of reference objects, which optionally can be surrounded by a cylindrical attenuating sleeve for image quality enhancement, during scanning thereof, and (c) one or more computer systems operable to estimate the bulk density, RhoB, and effective atomic number, $Z_{eff}$, as data pairs per individual rock fragment (all slices per rock fragment) in digital images obtained from scanning the rock fragments, and output the results to at least one device to display, print, or store results of the computations. The material of the sleeve is selected based on the bulked density and effective atomic number so that the x-ray attenuation is in the same range as the rock fragments.

Computerized systems, computer readable media, and programs for performing the methods are also provided.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate some of the embodiments of the present invention and together with the description, serve to explain the principles of the present invention. The drawings are not necessarily drawn to scale. Like numerals in the drawings refer to like elements in the various views.

BRIEF DESCRIPTION OF DRAWINGS

FIG. 15 is a chart of porosity, materials, connected porosity, and permeability from SCAL computations performed on the subarea of the selected cutting indicated in FIG. 12 according to an example of the present invention.

DETAILED DESCRIPTION OF THE PRESENT INVENTION

Figure 1:
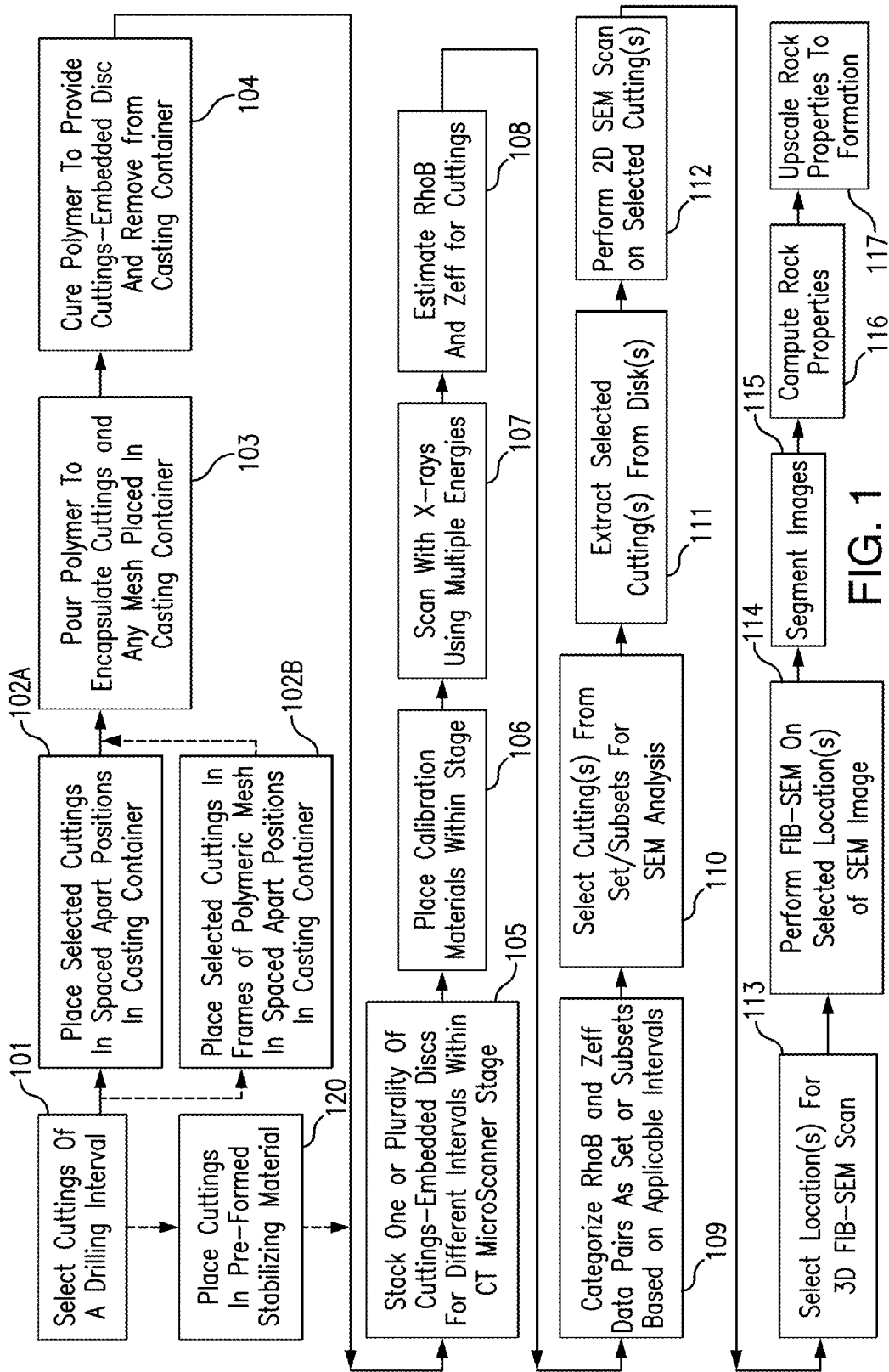
FIG. 1 is a flow chart describing a method according to an example of the present application.

The present invention relates in part to a method which allows organization of mass quantities of rock fragments such as drill cuttings obtained from one or more intervals of a well to more accurately categorize the cuttings to assist in selections of cuttings thereof for more detailed digital rock analysis. The method of the present invention makes it possible, for example, to screen through a large number of samples of rock fragments obtained from a single well interval or multiple well intervals to identify a sample or samples thereof for each interval that would be a better candidate(s) for use in more detailed analyses used to obtain estimates of rock properties of the formation or facies from which the rock fragments are obtained. For example, rock fragments can be selected using a method of the present invention which can better typify or otherwise have more relevant features or content for use in more detailed imaging systems, such as SEM, FIB-SEM or high resolution CT, that generate imaging data that can be used in computing and upscaling rock properties of interest. The method of the present invention thus can reduce or avoid drawbacks and inaccuracies which can arise from use of more randomly selecting rock fragments for such detailed analyses.

The method of the present invention, for example, can allow the organization of a mass quantity of rock fragments based on bulk density (RhoB) and effective atomic number (Zeff) data plots generated for rock fragments obtained from one or more intervals, based on multi-energy X-ray CT scans of the rock fragments. Unique rock fragment sample preparation techniques and systems are provided which can allow the method to be implemented at the same time on rock fragments from separate intervals of the same well. The bulk density and atomic number data plots generated for rock fragments obtained from different intervals can be displayed as different families or subsets on the same bulk density versus effective atomic number plots to show the distribution and amounts of data pairs within each family or subset. This integrated manner of outputting and presenting the results can facilitate the selection of rock fragments amongst the various intervals, such as for identifying better or more desirable candidates for more detailed analyses, such as by SEM/FIB-SEM.

The present invention relates in part to a method for processing rock fragments for computer tomographic scanning wherein a plurality of rock fragments, such as drill cuttings, can be positioned in space positions in a stabilizing material to provide a rock fragments-embedded carrier. A multi-energy X-ray CT scan can be performed on the rock fragments-embedded carrier comprising the plurality of rock fragments with at least 3 reference objects. The stabilizing material can be a pre-formed material or a material formed in-situ that can hold the rock fragments in a fixed position relative to each other during pre-scan handling and the scanning thereof. The stabilizing material can be a material that can provide a stable unitary mass or structure in which the rock fragments can be positioned in place relative to each other. The stabilizing material can be a material that can be digitally distinguished or removed with respect to results of multi-energy level scans performed on the rock fragments while placed in the stabilizing material.

The present invention further relates in part to a method which allows for the output of multi-energy computer tomographic (CT) scanning of rock fragments to provide information that is valuable at least because clusters (families) of individual rock fragments within a given depth interval can be identified which have similar density and atomic number, such as seen from a Dual Energy CT scan. Bulk density (RhoB) and effective atomic number ($Z_{eff}$) data plots can be generated for rock fragments obtained from a depth interval based on the dual-energy X-ray CT scans of the rock fragments. The data plotted in the bulk density and atomic number data plots generated for rock fragments can be categorized as different clusters or families. Such clusters can indicate different facies of the rock. The occurrence frequency distribution of rock fragments among clusters can describe the occurrence frequency distribution of the identified facies in the given depth interval. Repeating this analysis through all of the depth intervals can provide a log that displays this frequency distribution of facies along the entire well. This log can assist in the interpretation of formations down hole and allow the interpreter to also correlate rock fragments within a depth interval to rock fragments within a neighboring interval. The "occurrence frequency distribution" referred to herein also may be characterized as a population frequency distribution, and the "occurrence frequency" also may be characterized as a population frequency.

The present invention further relates in part to a method for determining a bulk property of a depth interval of a rock formation by using a determined physical or chemical property of rock fragments, such as drill cuttings, of different facies in the depth interval, and the frequency distribution of each of the different facies in the depth interval. The method can include obtaining a sample of a depth interval of a rock formation, for example, a sample made up of a plurality of rock fragments, such as drill cuttings. The plurality of rock fragments can then be separated into a plurality of clusters, and each rock fragment from the sample can be classified as a member of one of a plurality of clusters (families). As indicated, such clusters can indicate different facies of the rock. The discussion herein refers to facies in this respect. The plurality of rock fragments can make up a plurality of different facies, for example, two or more, three or more, or four or more different facies. A physical or chemical property of at least one exemplary or representative rock fragment of each of plurality of the different facies can then be determined. One or more rock fragments per facies can be analyzed for this purpose for a plurality of the scanned clusters for which the indicated bulk density and effective atomic number data plots were produced, and not every cluster necessarily needs to be analyzed for a property determination thereof. The same physical or chemical property can be determined for one or more representative rock fragments of the clusters. In some cases, the determining can involve determining the physical or chemical property of a plurality of rock fragments of each of the different facies and averaging a value of the physical or chemical property to determine an average property for each of the different facies.

Data that is unexpected can be verified and outlier data, such as outlying data points on a graph, can be eliminated if the determined property does not fit into an expected range of values, for example, if it does not fit into a range of values determined based on deeper or shallower depth intervals of the same rock formation, and/or based on a range of values determined for the same or a similar depth interval of a neighboring rock formation. By neighboring, what is meant is within 50 yards, within 100 yards, within 1000 yards, or within a half a mile, for example.

For each of the different facies in the sample, the frequency distribution of rock fragments of that facies can be calculated based on the total number of rock fragments in the sample and the total number of rock fragments of each of the different facies, in the sample. A bulk property of the depth interval can then be determined based on the determined physical or chemical property of the rock fragments of the different facies and the frequency distribution of each of the different facies.

The rock formation can be a subterranean rock formation, for example, into which an oil or gas well might be drilled. In some cases, the bulk property to be determined can be bulk density, average porosity, average total organic content, and/or average porosity associated with total organic content. In some cases, the method can further involve obtaining a sample of a different depth interval of the rock formation and using the same or a different method to determine a bulk property of the different depth interval. Like with the sample taken from the first depth interval, the bulk property determined can be compared to a bulk property previously determined for the same depth interval of a neighboring rock formation, and the bulk property determined can be verified if it is about the same as the bulk property previously determined for the neighboring rock formation.

An analysis of one or more rock fragments, such as drill cuttings, selected from each of the clusters of interest within a given depth interval can be performed using, for example, scanning electron microscopy (SEM), focused ion beam-SEM (FIB-SEM), CT-scanning, digital rock physics (DRP) techniques, petrographic techniques, or combinations of these or any method applicable to an individual rock fragment. As indicated, the data obtained from such an analysis can then be considered representative of the entire cluster from which the rock fragments were selected. For example, if a selected representative rock fragment of a cluster is determined to have a particular property value, that particular property value of the selected rock fragment can be used as the property value applied to all the other rock fragments of the same cluster in calculations of mean property values for the given depth interval. Or, as indicated, the property can be determined for a plurality of different rock fragments of a given cluster (e.g., 2, 3, 4, 5, or more), and an average value thereof can be calculated and used as representative of the entire cluster. Combining the data values resulting from analysis of individual rock fragments with rock fragment frequency distribution among clusters can provide a frequency distribution (histogram) of property values within the given depth interval. From this distribution, various statistical measures can be computed, which can provide a statistical upscaling of the rock properties. For example, if clusters based on such analysis can be classified as "pay" or "non-pay," then the sum of pay clusters' frequency becomes a measure of net-to-gross ratio.

One example can be obtaining porosity (e.g., average porosity), total organic content (TOC), density, and/or porosity associated with TOC values, within an individual rock fragment. After performing this analysis for a representative rock fragment selected from each cluster identified in a given depth interval, and combining the values with the rock fragments frequency distribution, the frequency distributions (histograms) of these values can be obtained within the depth interval or range. The mean porosity of the depth range, its mean TOC, and so forth, can be calculated. Clusters can be classified, such as those with high porosity and/or high TOC according to one or more selected criterion value(s), as "pay," and other clusters not meeting the selected criterion value(s) can be classified as "non-pay," and the depth interval's net-to-gross ratio can be calculated as a sum of the frequencies of the pay clusters.

For purposes of the present invention, the "rock fragments" can be rock samples obtained during drilling or other extraction activities, such as in or near a well site or potential well site, or other locations. For purposes of the present invention, "cuttings" can refer to drill cuttings obtained during the drilling of a wellbore through subsurface formations. Information on how drill cuttings can be obtained or recovered from wells for use in digital rock physics is generally known. For example, assignee's U.S. Pat. Nos. 8,081,796 and 8,155,377, and the assignee's U.S. Provisional Patent Application No. 61/535,601 (Ganz), published as U.S. Patent Application Publication No. 2013/0073207 A1, provide information in this respect, which patents and patent application are incorporated herein in their entireties by reference. For example, drill cuttings can be extracted from a drilling fluid by means of a shale shaker or similar device. The drill cuttings can be classified and grouped based on the time that they arrive at the surface. Drill cuttings can be grouped such that the downhole coordinates from which they were produced are estimated. The grouped drill cuttings can be stored in a bag, canister or similar device for further processing. Optionally, the drill cuttings then can be further classified by size. The depth interval or drilling interval from which cuttings are collected and stored in the bag or other container for further processing can be, for example, about 10 feet, from about 10 feet to about 50 feet, or from about 20 feet to about 30 feet, or another distance or range of distances.

It should be understood that drill cuttings are only one example of samples of rock formation that may be used with the present invention. Any other source of a rock formation sample, e.g., micro-cores, crushed or broken core pieces, sidewall cores, outcrop quarrying, and the like, may provide suitable rock fragment samples for analysis using methods according to the invention. Consequently, the invention is not limited in scope to analysis of drill cuttings. Drill cuttings are used for sake of illustration in examples provided herein. As indicated, micro-cores can be used as the rock fragment samples. Micro-cores can be generated continuously during drilling with drill bits available in the industry, wherein a micro-core broken by the bit can be carried to the surface up the annulus along with the drilled cuttings. The micro-core sizes can have shapes with dimensions that can be determined in part by the drill bit, and can be from about 5 mm to about 25 mm in diameter and from about 6 mm to about 50 mm in length, or other sizes. It nevertheless will be appreciated that the ability to apply the method and system of the present invention to cuttings can be particularly advantageous for the reasons indicated herein. For example, cuttings can be obtained from many wells for which cores are not available or readily available. Further, when a plurality of rock fragments are obtained from the same drilling interval for processing in a method of the present invention, the rock fragments can all be the same type, such as all drill cuttings, or all micro-cores, and so on, or combinations of different types of rock fragments obtained for the same drilling interval can be used.

Referring to FIG. 1, a process flow is illustrated which includes initial selection of cutting samples from a drilling interval (101), cutting preparation-related steps or step for multi-energy X-ray CT scanning (102A (or 102B), 103, and 104; or 120), a step related to placement of a cuttings-embedded carrier or stack of such carriers in a CT scanner stage (105), multi-energy X-ray CT scanning related steps (106-107), cutting categorization and selection steps (108-110) based on bulk density (RhoB) and effective atomic number (Zeff) estimated for the cuttings based on the scanned images thereof, selected cutting extraction (separation) from its polymeric carrier (111), and further detailed analyses on the extracted cutting and rock property computations and upscaling (112-117). A method of the present invention can be based on a subset of these steps which would not require all of them. For example, the progression of the steps up to the categorization of the bulk density and effective atomic number data pairs and the capability of making an enhanced cutting selection based thereon for more detailed analysis (109-110), is an advantageous and useful feature of the present invention.

With respect to step 101 in FIG. 1, cuttings can be visually selected that are isometric in dimension and which appear to accurately describe the entire sample of all cuttings within the interval relative to abundance. For purposes herein, "isometric" means a three-dimensional shape that has a maximum dimension that is not significantly larger than the minimum dimension of the shape, e.g., a shape that not flake-like or shavings. For example, the cuttings can have a maximum shape dimension/minimum shape dimension ratio of from 1 to about 5, or other values that do not relate to flake-like or shaving shapes. Isometric samples can provide better imaging within a CT scanner as opposed to a sample that is not isometric in shape. Further, the cuttings used in the methods of the present invention can be the original cuttings obtained from the well or subsamples obtained from the original cuttings. The cuttings can have a maximum diameter, for example, of from about 0.5 mm to about 5 mm, or from about 0.7 mm to about 4 mm, or from about 0.8 mm to about 3 mm, or from about 1 mm to about 2 mm, or other sizes. As will be discussed in greater detail herein, the size of the cuttings can be coordinated with 1 mesh opening size of an optional mesh type holder that can be used with the cuttings in a method of the present invention.

Figure 2:
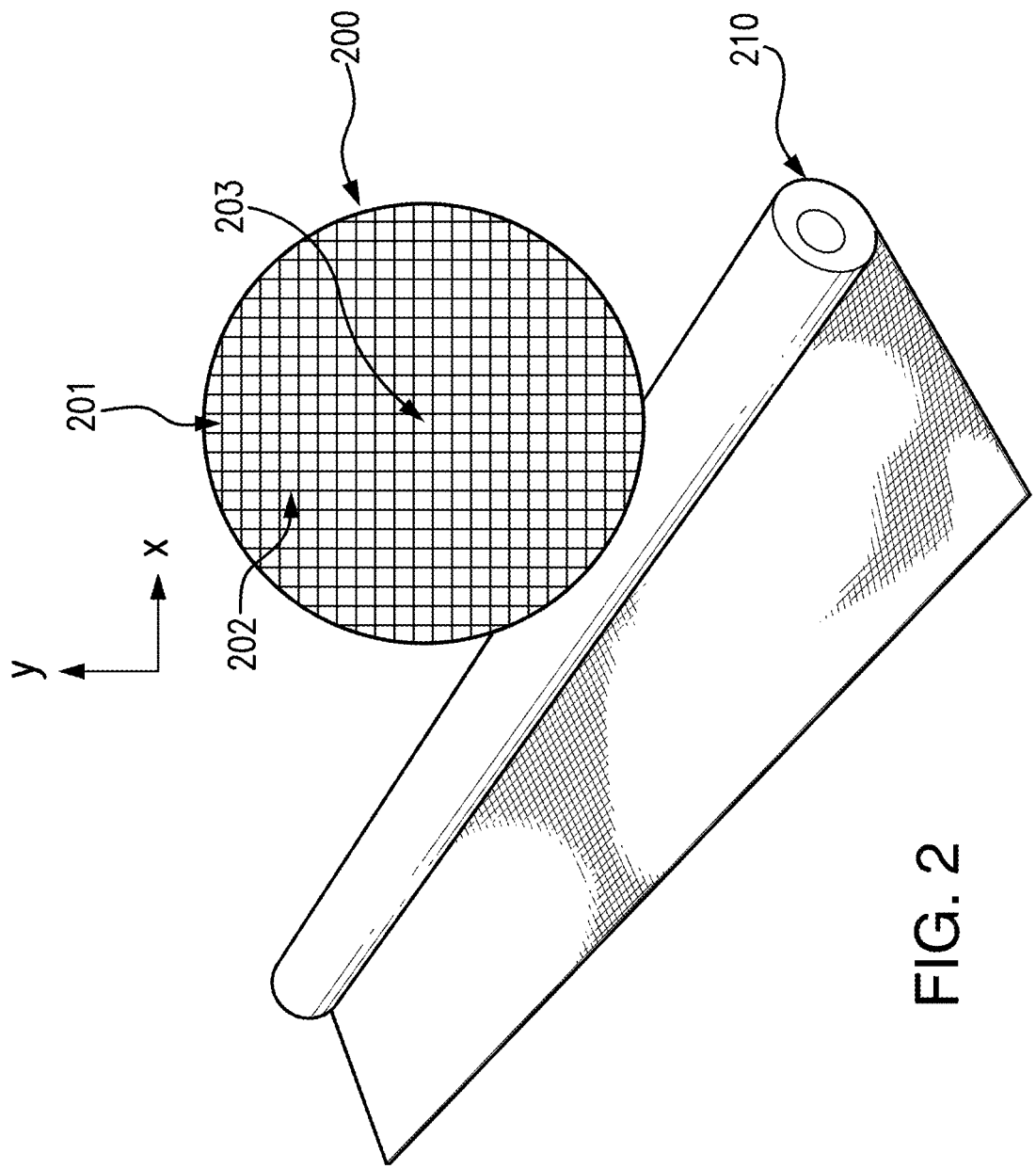
FIG. 2 is a top view of a mesh which can be used for holding cuttings in spaced apart locations according to an example of the present application.

In step 102A, cuttings are placed in a casting container in spaced apart locations with respect to each other on the inner bottom of the container, such as part of their preparation for CT scanning, such as described herein. This placement of the cuttings in the container in spaced apart locations can be done individually. The placement of the cuttings in the container can be done in a way that the cuttings are spaced apart as placed, or can be done by depositing the cuttings onto the bottom of the container in possible contact with each other and then moving them into spaced apart locations. A stabilizing material for the cuttings can be formed in-situ after depositing the cuttings in the container, such as by use of a hardenable material, such as a hardenable polymer material, as an encapsulating material. In alternative step 102B to step 101A, a polymeric mesh or screen-like material can be used to assist in sample holding, categorizing, and the spacing of the cuttings in the canister as part of their preparation for CT scanning, such as described herein. An example of the mesh is shown in FIG. 2. Mesh 200 is a polymeric material that has polymeric fibers, strands, or other small diameter elongated members 201 and 202 arranged to intersect in a regular pattern that defines openings 203 which have a substantially uniform gap size. Polymeric mesh can be commercially obtained, for example, in roll forms 210 that can be unwound to provide substantially planar lengths or strips of the material from which mesh pieces can be cut or punched. The mesh can be cut into discrete pieces having circle shapes, for example, but are not limited to that shape. The circles can have sizes, for example, of from about 5 mm to about 50 mm, or from about 10 mm to about 45 mm, or from about 15 mm to about 35 mm, or from about 20 mm to about 30 mm, or about 25 mm, or other sizes. This dimension may be only limited as a practical matter by the limitations of the scanner that is being used. If an objective allows for a larger Field of View (FOV) for scanning, larger diameter cups with larger diameter mesh inserts may be used. The mesh polymer can be, for example, a thermoset or a thermoplastic material. The mesh polymer can be, for example, epoxy resin, polypropylene, polyethylene, or other polymeric materials. As will be discussed in more detail, it can be beneficial to use a mesh polymer that is the same or similar to a resin used to embed and encapsulate the cuttings in a subsequent step of the method, as similar polymeric materials can attenuate x-rays at a similar rate. Further, the images from the multi energy X ray CT scan of the cuttings and mesh can have their dynamic range set in such a way that allows both the epoxy resin and mesh to be digitally removed from the image leaving only the cuttings before calculations (e.g., this can be due to the large difference in density and atomic number of both the mesh and epoxy (similar) from the samples encapsulated within). This can result in better imaging of the cuttings since the polymeric mesh and encapsulating resin will not interfere with the CT values in the cuttings. Individual cuttings from a sample interval can be fitted individually into individual separate frames within the plastic mesh. As indicated, the size of the cuttings can be coordinated with the mesh opening sizes of the mesh used to hold them. For example, knowing the sizes of the cuttings to be analyzed, a mesh can be selected that defines mesh openings which having sizes which allow a cutting to be manually wedged into a single mesh opening while gripped by the surrounding grid that defines that mesh opening. The mesh opening can have a smaller size than the dimension of the cutting to be wedged into and gripped therein. As can be seen in FIG. 2, the mesh can define a regular organized grid of openings and these grid openings can have x-y coordinates assigned to them, which can be used to track the respective locations of particular cuttings throughout the method while the cuttings are retained in the mesh. The number of cuttings that can be placed in mesh, if used, is not particularly limited other than by the number of mesh openings or frames presented by the mesh used. For example, from about 1 to about 50 cuttings, or from about 5 to about 40 cuttings, or from about 10 to about 30 cuttings, or other numbers of cuttings, having a size of from about 1 mm to about 2 mm, may be fitted into openings of a 25 mm (1 inch) circular mesh piece. Other numbers of the cuttings in the mesh may be used. The addition of known materials for orientation can helps improve sample selection after multi-energy CT scan processing.

As indicated in step 103 of FIG. 1, the cuttings placed in a casting container in a spaced apart arrangement, without a mesh or with a mesh used for placing the cuttings therein, can be further stabilized and formed into an isometric shape that is convenient for handling and analysis in methods of the present invention by encapsulating and embedding the cuttings in a polymer while in the spaced apart arrangement, such as placed in the canister without mesh or in mesh if used. As indicated, cuttings individually can be placed on the bottom of a casting container in spaced apart locations thereon, or a mesh with cuttings held in positions therein can be placed inside a casting container, prior to introducing an encapsulating material. The casting container can be a cylindrical cup or other open-mouthed container. For example, the mesh, if used, and cuttings can be placed on the internal bottom of the container. To fit inside the cylindrical casting container, the mesh can be cut into a circle of equal or smaller diameter relative to the opening defined by the casting container to fit within the sample cup. The mesh, if used, can be cut before or after placing the cuttings therein, as long as the trimmed piece includes the cuttings to be analyzed. The hardenable polymer can be poured into the casting cylinder in amount sufficient to surround and embed the cuttings, and any mesh used. The flow of the encapsulating polymer can be controlled to reduce or avoid moving the cuttings around when contacted by the polymer so that the cuttings remain spaced apart after been covered by the polymer. The hardenable polymer can be a curable thermosetting resin or a thermoplastic. Curable epoxy resin can be used as the hardenable polymer, or other hardenable resins. For example, an epoxy resin which is already flowable can be used, and when it is wanted to cure it, a catalyst is added and mixed that begins a chemical reaction within the epoxy resin that will cause it to cure over the designated cure time for that given epoxy. UV-curable resins can be used. Isocyanate resins can be used. If a thermoplastic is used, the material may be softened with heating to render it sufficiently pourable and flowable, and upon cooling it can harden in place. Once the cast resin hardened, a cuttings-embedded carrier is formed that can be removed from the casting cylinder and used in further processing according to methods of the present invention.

Figure 3:
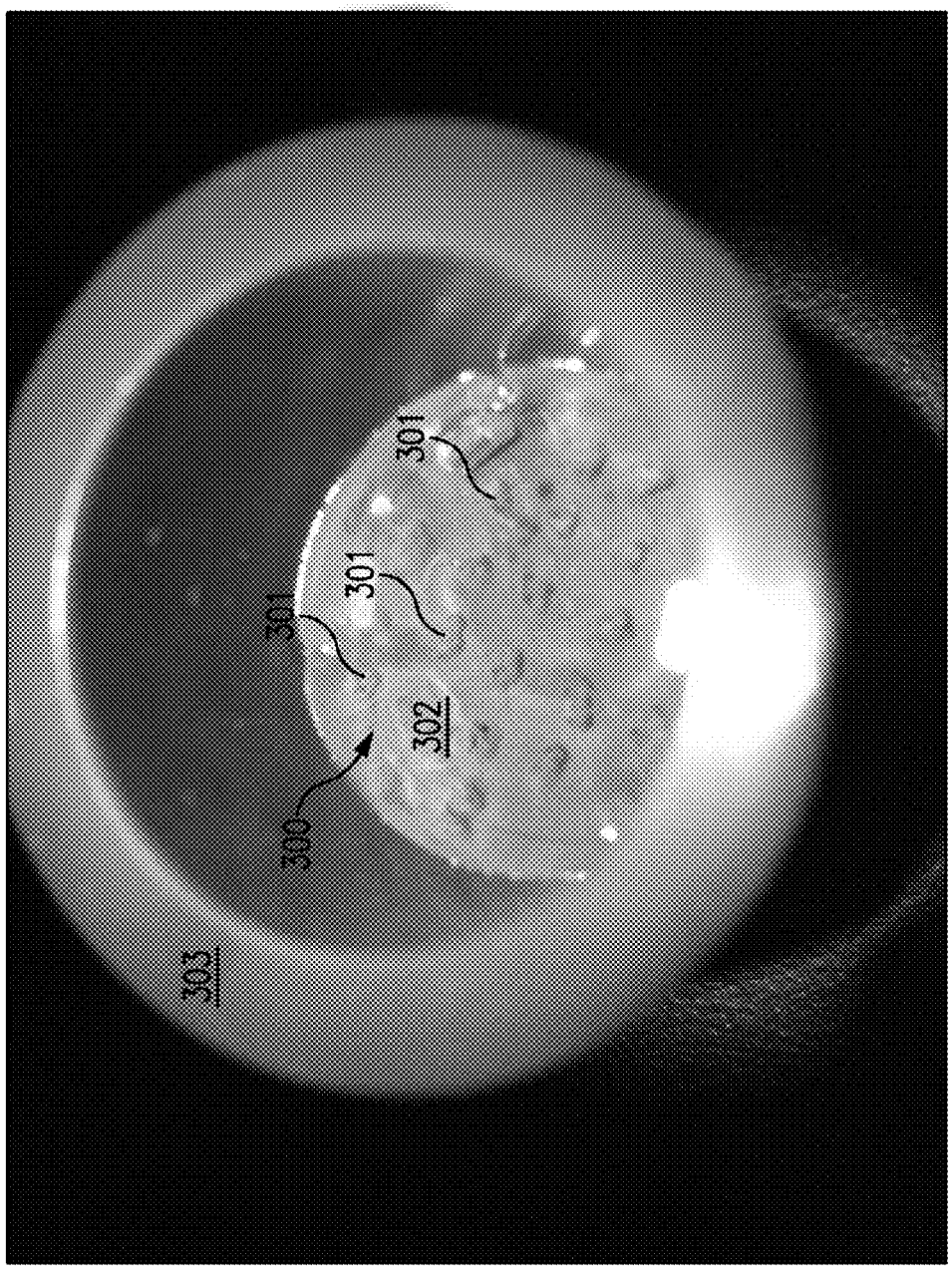
FIG. 3 is a photograph of casting container containing a cuttings-embedded carrier according to an example of the present application.

As illustrated in FIG. 3, for example, a cylindrical cup 303 is shown which contains a cuttings-embedded carrier 300 which has a plurality of cuttings 301 embedded within epoxy resin 302. The mesh, if present, is not visible in this view. The epoxy/resin has been poured within the cylindrical cup over the cuttings and any mesh and to mount the cuttings. Mounting of the cuttings can be done under vacuum or not. This choice can depend on the type of epoxy/resin used, and sample lithology. Vacuum can be used, for example, where it is desirable to use a resin which also infiltrates into pores of the cuttings. If pore infiltration is not desired or needed, a more viscous resin can be used as long as it is flowable enough to completely surround the cuttings, and any mesh, and displace all or essentially all air. The epoxy/resin is then cured or allowed to cure. The cure time can depend on the type of epoxy used, temperature, UV-light exposure, catalyst loading, and the like. Once cured, the cuttings-embedded carrier is removed from the sample cup. The casting cup material is not limited as long as it can release the cuttings-embedded carrier for removal, for example, an epoxy cup or other material which will release an epoxy-encapsulated cuttings and any mesh. A release agent also can be used, which can be swabbed over the inside of the cup before placing the cuttings and any mesh within the cup and before pouring the epoxy resin. The cuttings-embedded carrier that can be removed from a cylindrical casting cup in this illustrated manner can have a disc shape or cylindrical chip shape. Cylindrical shaped objects can provide better CT scanning results, so this shape can be desirable for the cuttings-embedded carriers, but is not limited thereto. The cuttings-embedded carrier, such as a disc shaped one, can have a thickness, for example, of from about 2 mm to about 5 mm, or from about 2 mm to about 4 mm, or from about 2 mm to about 3 mm, or other thicknesses. The embedding resin or plastic provides a uniform physical thickness for separating the cuttings of one cuttings-embedded carrier from others, which as described herein, can be stacked together for scanning at the same time and integrated analysis of the results thereof in methods of the present invention.

Alternative preparation (e.g., pre-scanning) methods for the cuttings can include, for example, excluding the use of mesh with the recognition that it may be more difficult to pour encapsulating resin onto the cuttings and keep them in a fixed position. An x-ray absorbable filler may be used with the epoxy or other polymeric encapsulating material, for example, which can improve x-ray CT. As another alternative preparation method, a pre-formed stabilizing material can be used to hold the plurality of cuttings or other rock fragments in spaced apart positions relative to each other. As shown in FIG. 1 (and FIG. 16A), as another option, the selected drill cuttings or other rock fragments of a drilling interval in step 101 (or step 601 respectively) can be collectively positioned in a pre-formed stabilizing material in step 120 (or step 625 respectively), instead of forming the stabilizing material around the rock fragments in-situ via indicated steps 102A or 102B, 103 and 104 (or via steps 602A or 602B, 603, and 604 respectively). The resulting cuttings-embedded carriers, such as disc shaped carriers or other shaped carriers formed via step 120 (or step 625) can be used in step 105 (or step 605). The spaced apart locations of the cuttings can be two-dimensional or three-dimensional in the stabilizing material. A pre-formed stabilizing material used in this manner can be putty, bone, foam, or other stabilizing materials. The use of a pre-formed stabilizing material to hold the rock fragments can eliminate the need to use a casting container shown in an example herein.

Figure 4:
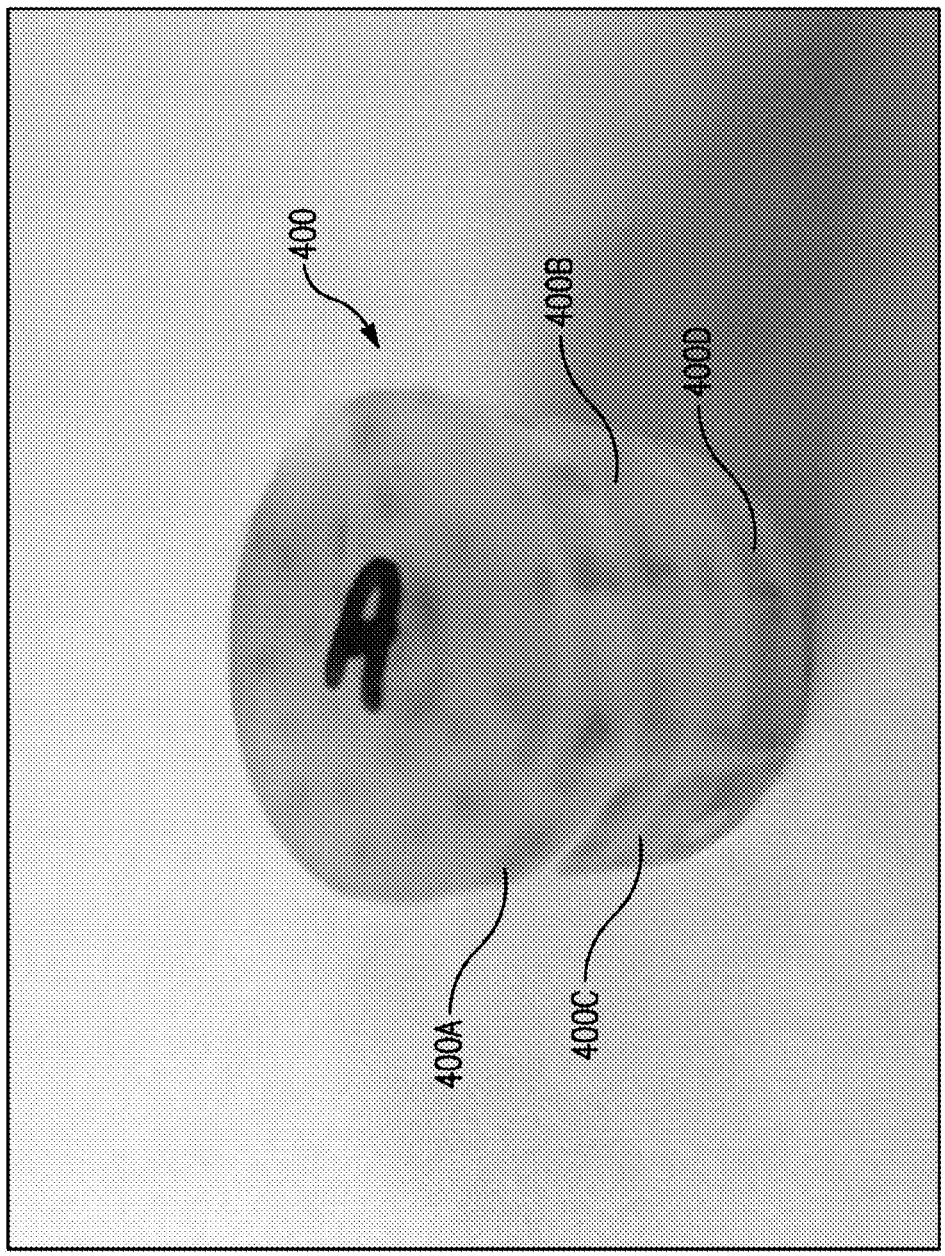
FIG. 4 is a photograph of a stack of cuttings-embedded carriers according to an example of the present application.

As indicated in step 105 of FIG. 1, a plurality of cuttings-embedded carriers can be formed in a similar manner for different lots of cuttings obtained for same or different intervals of the well. Then, these different carriers having similar geometries but different sets of cuttings can be stacked for placement in a scanning stage of a CT scanner. For example, FIG. 4a shows a stack 400 of four different cuttings-embedded carriers 400A, 400B, 400C, and 400D. Other numbers of the carriers can be stacked together, e.g., from about 2 to about 25, or from about 5 to about 20, or from about 10 to about 15, or other numbers thereof. Although the method of the present invention can provide additional advantages when applied at the same time to multiple cuttings-embedded carriers stacked together for CT scanning and post-CT scanning analysis, the method also can be applied to a single cuttings-embedded carrier if desired. This method allows sample size (total number of cuttings) to be increased per multi energy X-ray CT scan. This can give the flexibility to either scan multiple intervals of cuttings within a single scan, or scan a larger distribution of cuttings for a single interval per multi energy X-ray CT scan. The unique cutting sample preparation techniques and systems of the present invention can be used, for example, to position cuttings obtained from the same interval in laterally (e.g., x-y) isometric positions relative to each other in a cylindrical carrier for CT scanning, such as multi-energy X-ray scanning. The preparation method further allows cuttings obtained from different intervals of the same well to be positioned isometrically vertically (e.g., z direction) relative to each other when the separate carriers are stacked into an overall cylindrical shape that can be placed in a stage of a CT scanner, such as multi-energy X-ray scanner. The cylindrical shape can reduce noise, which can provide better images and less artifacts. The multiple carriers in addition to the mesh adds dimension to categorize the cuttings.

Figure 5A:
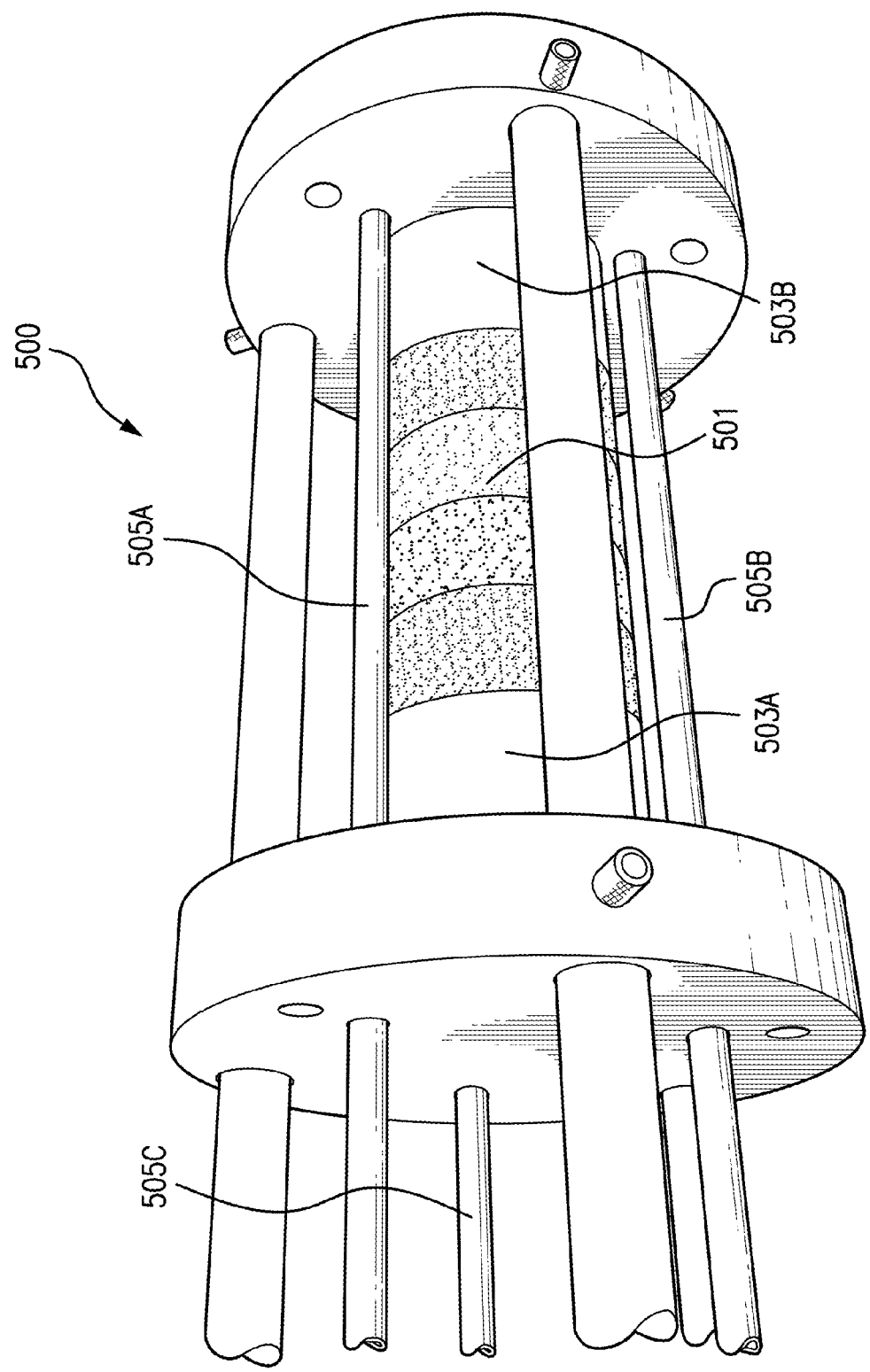
FIG. 5A is a photograph of a scanner stage of a dual-energy (DE) CT scantier with a stack of cuttings-embedded carriers and reference objects positioned therein according to an example of the present invention.
Figure 5B:
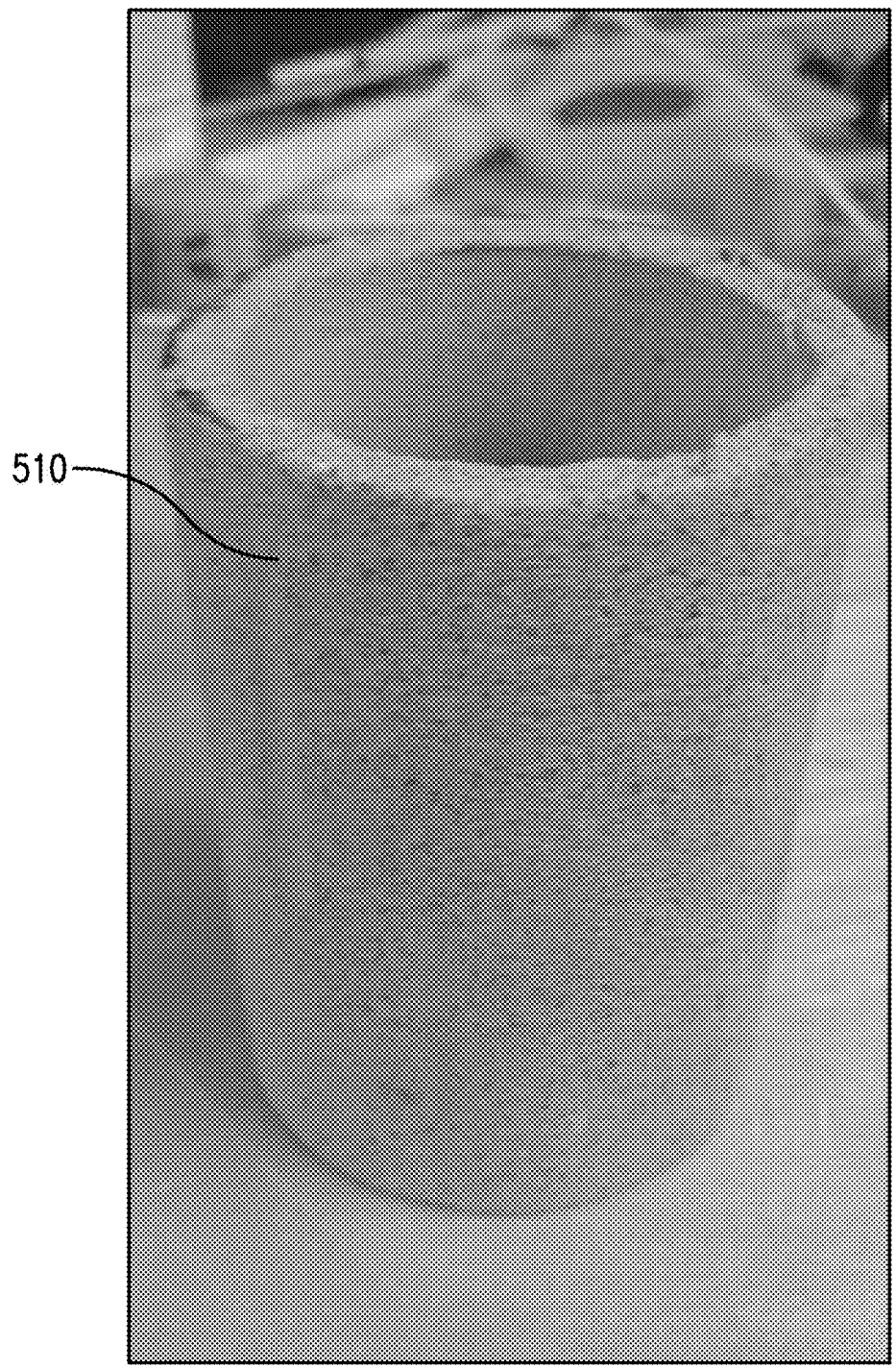
FIG. 5B is a photograph of an attenuating sleeve which can be used with the stage such as shown in FIG. 5A according to an example of the present application.

The cuttings-embedded carrier or stack of carriers can be placed in a stage of a CT scanner (105). Reference objects can be included within the stage with the carriers (106). FIG. 5A, for example, shows a scanner stage 500 of a dual-energy (DE) CT scanner with a stack of cuttings-embedded carriers 501 and at least three reference objects 505A, 505B, and 505C. With regard to the three or more reference objects, these objects can be liquid or solid materials such as polymers, metals, minerals or chemical compounds. Each of the reference objects can have a different effective atomic number and/or bulk density from each of the other reference objects. The reference objects are generally homogeneous and made of materials with known and different densities and effective atomic numbers. The density and atomic number values of the reference objects should cover the expected range of densities and atomic numbers in the target object under investigation. The types of materials, use, and arrangement of calibrations materials is further described, for example, in assignee's U.S. Provisional Patent Application No. 61/511,600 (Derzhi et al.), published as U.S. Patent Application Publication No. 2013/0028371 A1, which is incorporated herein in its entirety by reference. The components 503A and 503B, such as glass cylinders (or epoxy cylinders of the same epoxy used for sample impregnation), can be used to clamp the stack of carriers 501 there between in the stage. Also, the entire stage can have an attenuation sleeve positioned around the samples, calibrations rods, and the clamps (top and bottom cylinders). An attenuation sleeve 510 in this respect is illustrated in FIG. 5B. This sleeve can provide additional attenuation within the sample that can improve image quality within the multi-energy X-ray CT scan itself. Other components shown in FIG. 5A relate to structural components of the stage that are not important to the discussion of the method and system of the present invention.

The stack of cuttings-embedded carriers or single carrier, as positioned in the stage of the scanner, can then be scanned using a multi-energy X-ray CT scanner (107). The CT scanner can be used at a nominal resolution, for example, of from about 10 µm to about 50 µm, or from about 10 µm to about 45 µm, or from about 10 µm to about 25 µm, or from about from about 10 µm to about 15 µm, or other values. There is no specific theoretical limit on the lower limit size of the resolution. The cuttings-embedded carriers are scanned with X-rays using dual energies or more than two energies.

The CT values generated by the scanner are reconstructed for each energy scan. The cutting's CT values are separated from each other and embodying carrier using a threshold and other segmenting techniques. The CT values can be averaged for each cutting at each energy scan. The averaged CT values for each energy scan is processed to estimate bulk density, RhoB, and effective atomic numbers, Zeff, for each cutting in each cuttings-embedded carrier (108). Methods for reconstructing the data set and estimating the bulk density, RhoB, and effective atomic numbers, Zeff, for the cuttings, for example, by adapting the methodologies such as described in the indicated assignee's U.S. Provisional Patent Application No. 61/511,600 (Derzhi et al.), published as U.S. Patent Application Publication No. 2013/0028371 A1, which is incorporated in its entirety by reference, describes methods which can be used herein to calculate RhoB and $Z_{eff}$ from multiple energy, e.g., high and low energy, CT values. For example, a scan of the sample can be run, a 3D image is obtained with CT value for each voxel, similar to the method indicated in the incorporated application, and then all the voxels associated with each cutting can be taken and an average is calculated on them. Thus, each cutting can have an average value. This is performed for each different energy scan (e.g., high and low energy scans). So if a dual energy scan is performed, each of the cuttings has an averaged high and low CT value. These two values for each of the cuttings and each of the reference objects can be used to process and compute the bulk density and effective atomic number.

Figure 8:
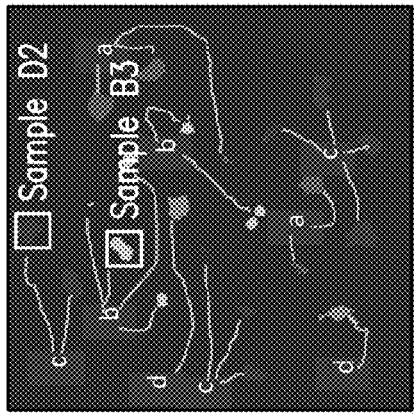
FIG. 8 is a density (RhoB) map of cuttings from the DE CT microscan of a cuttings-embedded carrier referenced in FIG. 6 according to an example of the present invention.
Figure 7:
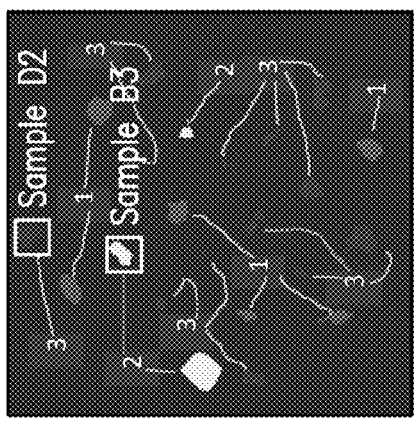
FIG. 7 is an effective atomic number (Zeff) map of cuttings from the DE CT micro scan of a cuttings-embedded carrier referenced in FIG. 6 according to an example of the present invention.
Figure 6:
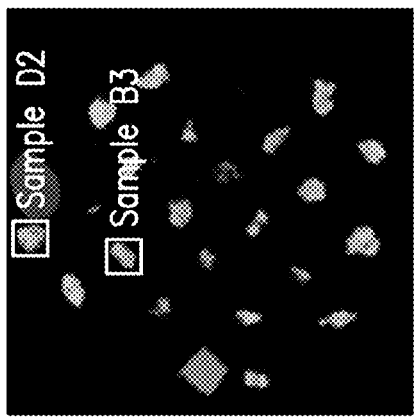
FIG. 6 is a CT image of cuttings scanned on the DE CT scanner referenced in FIG. 5A from which density and atomic number maps are calculated from according to an example of the present invention.

FIG. 6 shows a CT image of cuttings from which bulk density and atomic number maps are calculated, which are based on DE CT micro scans of cuttings obtained from four well intervals and prepared into a stack of carriers for scanning at the same time as described herein. FIG. 7 shows an effective atomic number (Zeff) map of the cuttings from the DE CT micro scan of the cuttings-embedded carriers. FIG. 8 shows a density (RhoB) map of the cuttings from the DE CT micro scan of the cuttings-embedded carriers. Using the results from the DE Micro scan, a facies list based on both mineralogy and density on all of the cuttings can be created.

Figure 9:
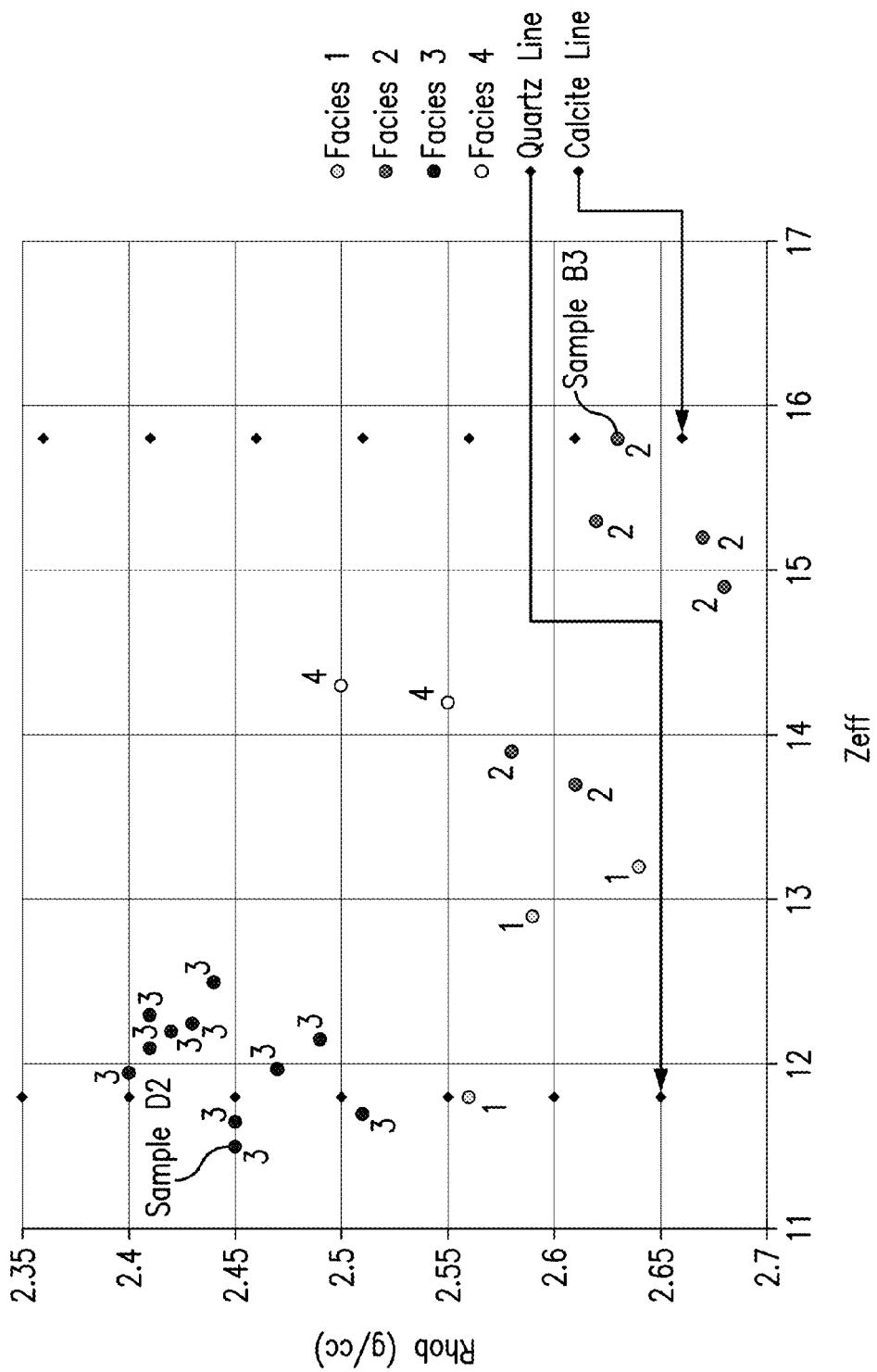
FIG. 9 is a plot of bulk density and effective atomic number for cuttings in different cuttings-embedded carriers ("facies"), which is used to identify subsets of the cuttings at each facies for selection of cuttings for further detailed analysis according to an example of the present invention.

For example, FIG. 9 is a plot of bulk density, RhoB, and effective atomic number, Zeff, for cuttings in different cuttings-embedded carriers ("families"). In FIG. 9, the bulk density, RhoB, increases in value along the y-axis from top to bottom. This plot allows for categorization of all the cuttings within a scan. The plot can allow for the selection of a representative or exemplary proper cutting for further analysis (e.g., step 110 in FIG. 1), such as using SEM, FIB-SEM or both (e.g., steps 112-117 in FIG. 1). The different clusters have corresponding data points (data pairs) numbered 1, 2, 3, and 4 in this illustration. These different clusters indicate respective "facies" in this illustration, as indicated in the figure. In FIG. 9, the data points of the different clusters have been labeled with identifying numbers adjacent to them so that the corresponding facies 1, 2, 3, or 4 can be understood. This categorizing of the bulk density, RhoB, and effective atomic number, $Z_{eff}$, data pairs into clusters can be done based on similar density and effective atomic number values. There is no theoretical limit to the number of facies that can be assigned as long as it does not exceed the total number of cuttings and can be discerned from the plot in FIG. 9. For example, the facies 1 subset tends to show higher density and lower Zeff, the facies 2 subset (which includes cutting B3) tends to show higher density and higher Zeff, the facies 3 subset (which includes cutting D2) tends to show lower density and lower Zeff, and the facies 4 subset tends to show higher density and higher Zeff relative to at least facies 3.

Further, although steps 108-109 in FIG. 1 (and steps 608-609 in FIG. 6A) illustrate the method using atomic number (Zeff values), the atomic number can be converted to photoelectric absorption cross section ($P_e$), and $P_e$ can be used in methods of the present application. Photoelectric absorption alternatively may be referred to as photoelectric effect index ("PEF"). $P_e$ (or PEF) may be calculated from atomic number (Zeff) by the equation: $P_e = (Z_{Eff}/10)^{3.6}$. Crossplots of RhoB and $P_e$ (or PEF) on Cartesian coordinates, for example, can be generated and used in methods of the present application, such as in a similar manner as shown herein for the crossplots of RhoB and Zeff.

Figure 11:
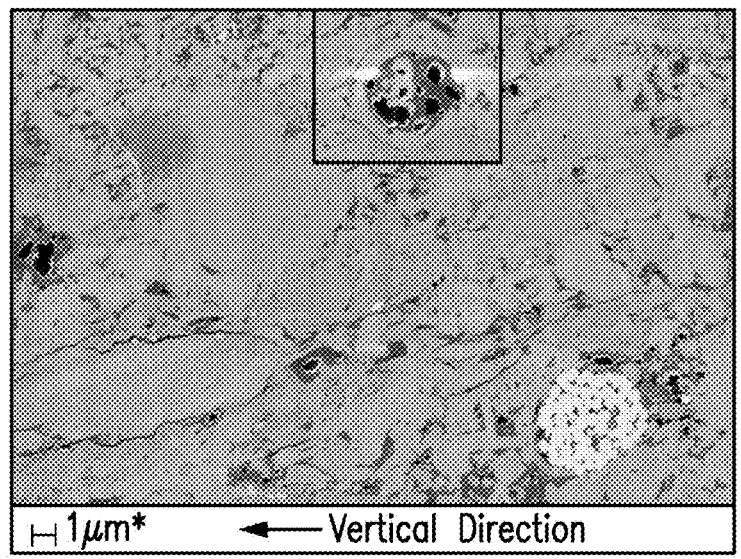
FIG. 11 is a SEM 2D image of sample D2 indicated in FIGS. 6-9 according to an example of the present invention.
Figure 12:
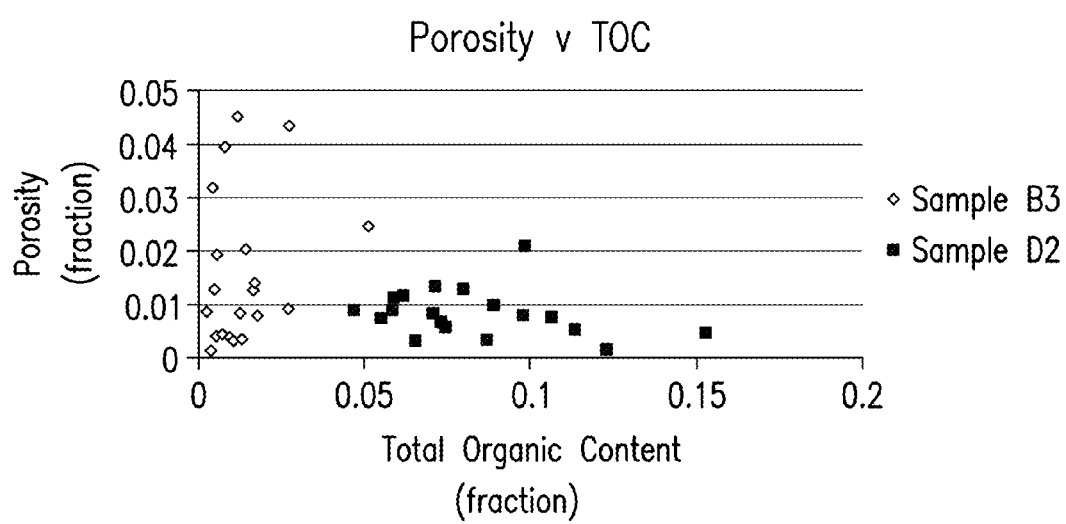
FIG. 12 is a plot of porosity and total organic content (TOC) estimated from 2D image analysis on the indicated selected samples B3 and D2 according to an example of the present invention.
Figure 13:
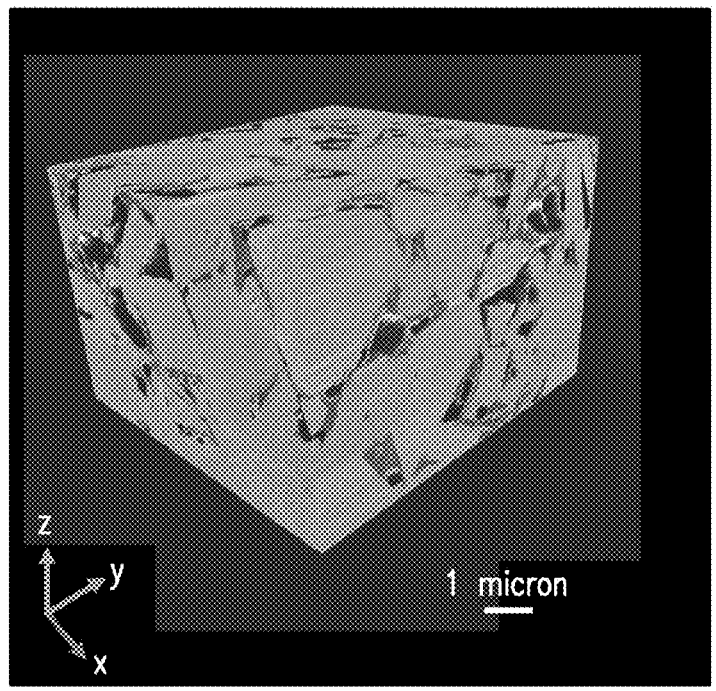
FIG. 13 is a 3D FIB-SEM scan image at 15 nm per voxel for the subarea identified by the square in FIG. 11 of FIB-SEM according to an example of the present invention.
Figure 14:
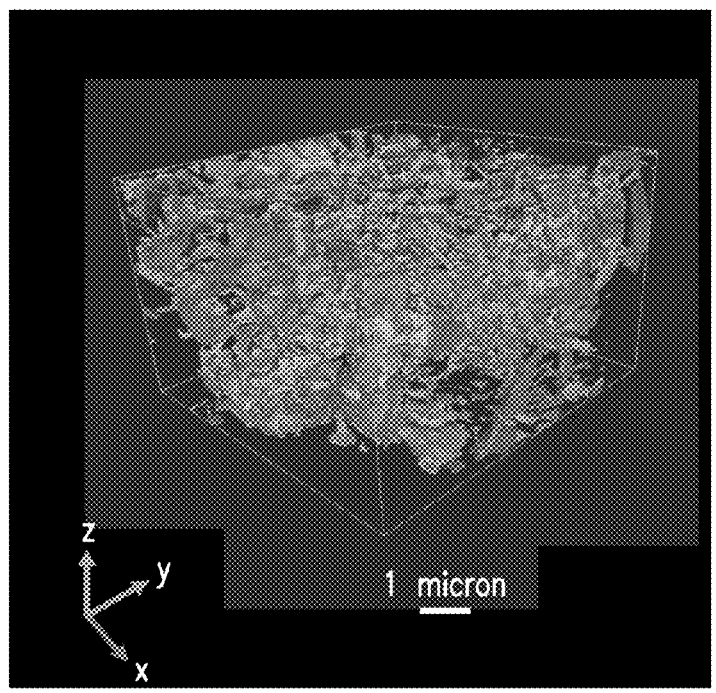
FIG. 14 is a 3D FIB-SEM scan image at 15 nm per voxel of selected contents of the subarea identified by the square in FIG. 11 of FIB-SEM according to an example of the present invention.

After Micro X-ray CT Analysis, 2D SEM analysis can begin on the selected samples (e.g., cuttings B3 and D2 in the above example provided herein) (112). Before SEM scanning can be performed, the selected cuttings are removed from the carriers. For example, the selected cuttings can be exposed by laser cutting and pulled out. The isolated cuttings are scanned in these steps. The 2D images shown in FIGS. 10 and 11, and the porosity versus total organic content plot shown in FIG. 12, based on the SEM analysis, provides information that verifies that the selection method used based on the plotting of bulk density versus effective atomic number, such as illustrated in FIG. 9, returns useful data about the cuttings pulled up from the well. For example, it can be plainly seen that cutting D2 is better candidate for detailed analysis than cutting (B3). Cutting B3 exhibits induced fractures (FIG. 10), such as man-made/drill-made fractures, and would not be recommended for computations of rock properties. Cutting D2 exhibits no induced fractures, and would be recommended for computations. FIG. 12 shows data points for about 20 SEM images taken at the same depth of the cuttings B3 and D2. FIGS. 13 and 14 show 3D voxel images obtained using a FIB-SEM for the subarea identified by the square in FIG. 11. FIG. 15 provides a chart rock properties computed from the analysis of the indicated subarea of cutting D2. The equipment used for the 3D scans can be, for example, a Focused Ion Beam-Scanning Electron Microscope (FIB-SEM). A method and system such as described by Carpio et al in U.S. Provisional Patent Application No. 61/547,090, published as U.S. Patent Application Publication No. 2013/0094716 A1, which is incorporated herein in its entirety by reference, or similar method and systems can be used to segment the 3D image. Segmentation can be used at least in part to identify pores, grains, organic content, and porosity associated with organic content in the images. Once the segmented images have been produced, rock properties can be computed.

In the methods of the present invention, the properties estimated for the cuttings or other porous media can be optionally upscaled to further estimate the properties of larger volumes of the porous media, such as rock facies or subterranean reservoirs. Special core analysis (SCAL) computations, for example, can be performed on the selected cutting to produce rock properties such as permeability, relative permeability, capillary pressure, and so forth. RCAL (Routine core analysis) computations also can be made. These types of values can be very important for understanding the best way to complete a well from a reservoir quality perspective. For example, SEM/FIBSEM properties on cuttings can be upscaled to the selected facies within the measured depth interval from which the cutting(s) originated.

The types of rock to which a method of the present invention can be applied are not necessarily limited. The rock sample can be, for example, organic mud rock, shale, carbonate, sandstone, limestone, dolostone, or other porous rocks, or any combinations thereof.

As indicated, U.S. Patent Application No. 61/511,600, published as U.S. Patent Application Publication No. 2013/0028371 A1, which is incorporated herein in its entirety by reference, describes methods which can be used herein to calculate RhoB and $Z_{eff}$ from multiple energy, e.g., high and low energy, CT values. The method for estimating the bulk density and/or effective atomic number of a target object can involve, for example, one or more of the following steps which can be performed once or multiple times:

i. performing a scan of two or more reference objects and three or more calibration objects,
ii. obtaining a functional relationship between bulk density error and effective atomic number using scan values from the reference objects and the calibration objects,
iii. performing a scan of the target object and the three or more calibration objects,
iv. obtaining uncorrected density and effective atomic number for the target object,
v. obtaining bulk density corrections using the functional relationship between bulk density error and effective atomic number from the reference objects, and the effective atomic number for the target object, and
vi. obtaining the corrected bulk density using the bulk density corrections. Additional details on this methodology are included in the indicated incorporated patent application publication herein.

Figure 16A:
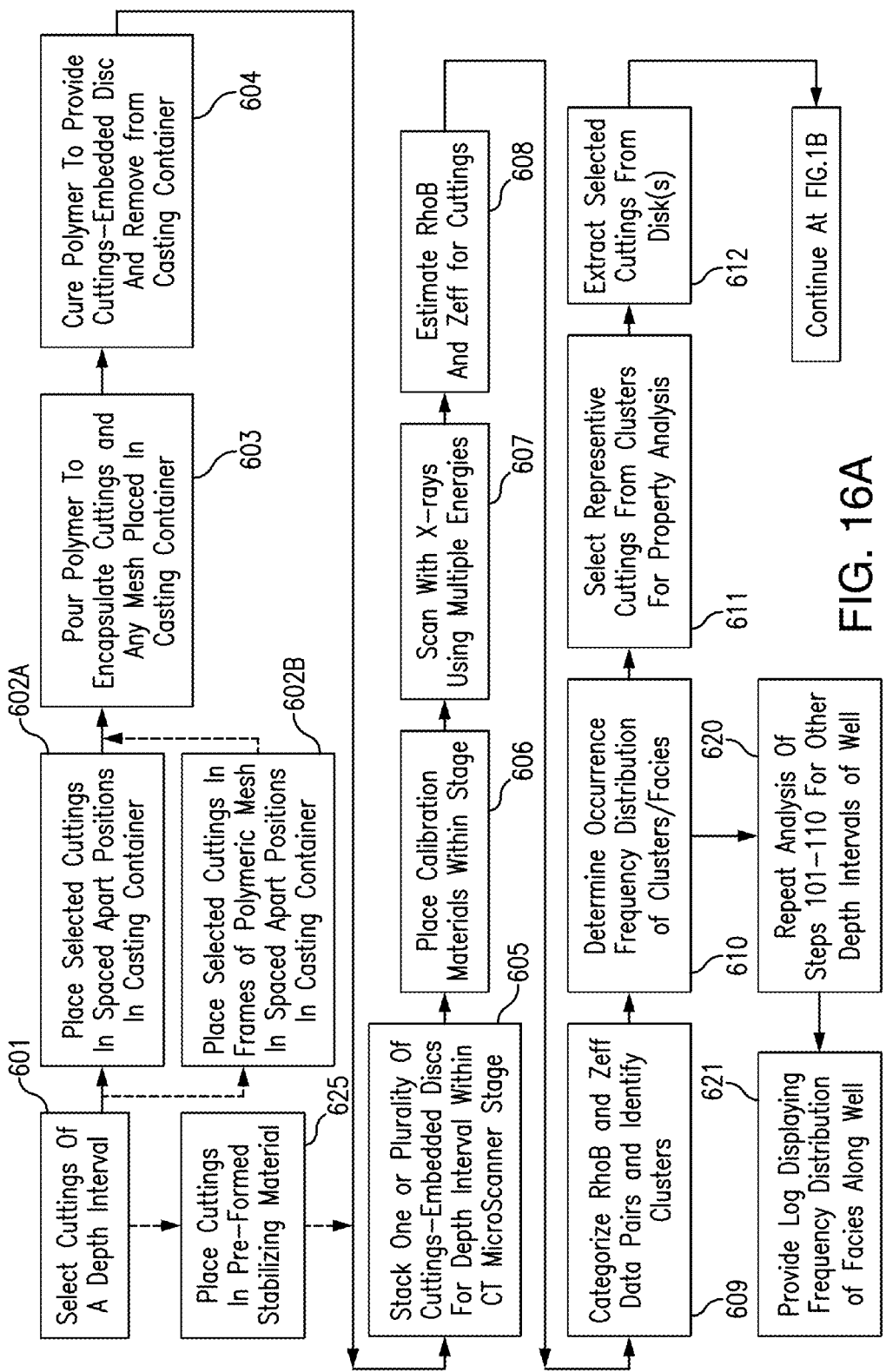
FIGS. 16A and 16B are a flow chart describing a method according to an example of the present application.
Figure 16B:
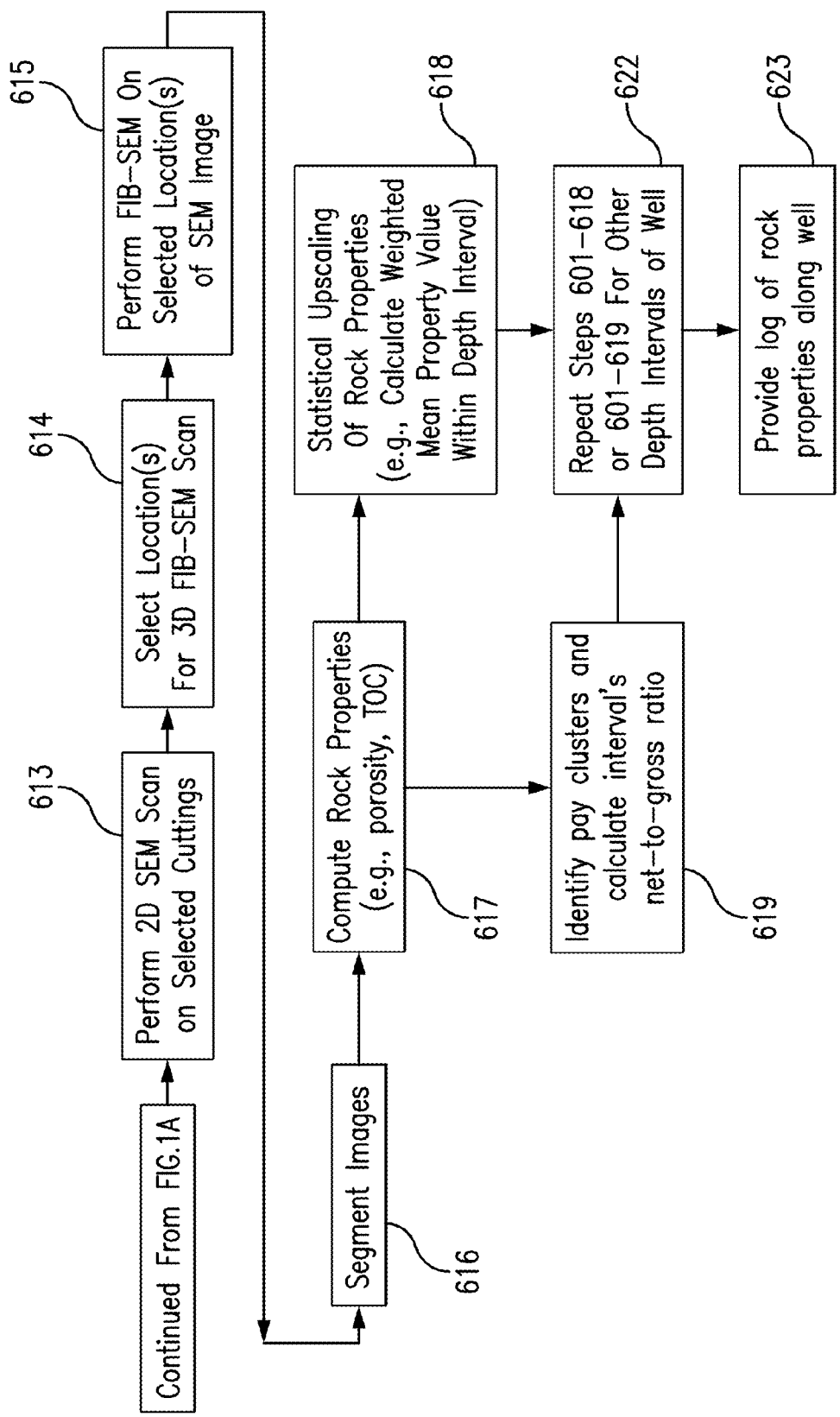

Referring to FIGS. 16A-16B, in another method according to an example of the present application, a process flow is illustrated which includes steps 601-623 and 625. The process flow as illustrated in these figures comprises an initial selection of cutting samples from a depth (drilling) interval (step 601), cutting preparation-related steps for multi-energy X-ray CT scanning (steps 602A (or 602B), 603, 604 and 605; or steps 625 and 605), multi-energy X-ray CT scanning related steps (steps 606-607), categorization of RhoB and Zeff data pairs and identification of clusters or families (step 609), a determination of occurrence frequency distribution for cuttings among clusters and facies (step 610), a step of selecting a representative cutting from each cluster based on bulk density (RhoB) and effective atomic number ($Z_{eff}$) estimated for the cuttings from scanned images thereof (step 611), a selected cutting extraction (separation) from its polymeric carrier (step 612), further detailed analyses on the extracted cuttings and rock property computations (steps 613-617), a statistical upscaling of rock properties, such as a calculation of a weighted mean property value within depth interval (step 618), an identification of pay clusters and a calculation of a depth interval's net-to-gross ratio (619), a repeating of the analysis of steps 601-610 after step 610 for different depth intervals along the well, such as through all of the depth intervals thereof (step 620), and providing a log that displays the frequency distribution of facies along the well, such as the entire well (step 621), a repeating of the analysis of steps 601-618 (after step 618) or steps 601-619 (after step 619) for different depth intervals along the well, such as through all of the depth intervals thereof (step 622), and providing a log that displays the frequency distribution of facies alone the well, such as the entire well (step 623). A method of the present invention can be based on a subset of these steps, and not all of the illustrated steps are required.

With respect to step 601 in FIG. 16A, cuttings can be visually selected that are isometric in dimension and which appear to accurately describe the entire sample of all cuttings within the interval relative to abundance. The cuttings can have an aspect ratio from about 0.2 to 1, or other values that do not relate to flake-like or shaving shapes. The cuttings can have the indicated maximum diameters. In step 602A in FIG. 16B, cuttings are placed in a casting container in spaced apart locations with respect to each other on the inner bottom of the container, such as part of their preparation for CT scanning, such as described herein. In step 602B, as an alternative, the indicated polymeric mesh or screen-like material can be used to assist in sample holding, categorizing, and the spacing of the cuttings as part of their preparation for CT scanning, such as described herein. As indicated in steps 603-604 of FIG. 16A, the cuttings placed in the casting container can be stabilized and formed into an isometric shape that is convenient for handling and analysis in methods of the present invention by encapsulating and embedding the cuttings in a polymer and then curing the polymer, without mesh or while retained in mesh. A cylindrical cup 303, such as shown in FIG. 3, can be used for forming a cuttings-embedded carrier 300 which has a plurality of cuttings 301 embedded within resin 302. The resin encapsulation and curing procedure used for this embodiment can be similar to that described for steps 103 and 104 of the method shown in FIG. 1. As indicated in step 605 of FIG. 16A, and similar to step 105 of the method shown in FIG. 1, a plurality of cuttings-embedded carriers can be formed in this similar manner for different lots of cuttings obtained for the same intervals, or different intervals, or both, of the well. Then, these different carriers having similar geometries but different sets of cuttings can be stacked for placement in a scanning stage of a CT scanner. The cuttings-embedded carrier or stack of carriers can be placed in a stage of a CT scanner (step 605). The indicated reference objects can be included within the stage with the carriers (step 606). The indicated FIG. 5A shows a scanner stage 500 of a dual-energy (DE) CT scanner with a stack of cuttings-embedded carriers 501 and at least three reference objects 505A, 505B, and 505C, which can be used for this example of a method according to the present application. The stack of cuttings-embedded carriers or the single carrier, as positioned in the stage of the scanner, can then be scanned using a multi-energy X-ray CT scanner (step 607). The CT scanner can be used at similar resolution as indicated for step 107 of FIG. 1. The cuttings-embedded carriers can be scanned with X-rays using dual energies or more than two energies, such as indicated for step 107 of FIG. 1. Averaged CT values generated for each of the energy scans can be processed to estimate bulk density, RhoB, and effective atomic numbers, $Z_{\it eff}$, for each cutting in each cuttings-embedded carrier (step 608), which can be similar to that indicated for step 108 of the method shown in FIG. 1.

FIGS. 6-9 can have similar relevance to this example of a method of the present application as indicated for the method shown in FIG. 1. Further, the clusters classified as facies 1-4 can be used to identify different respective facies of rock of the depth interval from which the cuttings are obtained. Occurrence frequency distribution can be determined for cuttings among clusters and the indicated facies (step 610). For example, by determining an occurrence frequency distribution of the cuttings with respect to the clusters, based on a frequency of cuttings in each cluster of the clusters and the total number of cuttings, the occurrence frequency distribution of the cuttings can be said to correlate with the occurrence frequency distribution of the identified facies in the depth interval. As indicated, the analysis of steps 601-610 can be repeated for different depth intervals along the well, such as through all of the depth intervals thereof or a range of different intervals (step 620). A log can be provided that displays the frequency distribution of facies along the well, such as the entire well or other ranges of intervals of the well (step 621).

As indicated, a physical or chemical property of at least one exemplary or representative drill cutting of each of the different clusters or facies of a depth interval can be calculated after the identification of the clusters. After Micro X-ray CT analysis, for example, 2D SEM analysis can begin on selected cuttings of the clusters for this purpose. At least one representative cutting can be selected from each cluster for the analysis related to property calculation (step 611). In some cases, a plurality or all of the cuttings of a cluster also may be selected as being the representative cuttings of a given cluster. If multiple cuttings from a cluster are selected, then the property determining can involve averaging a value of the physical or chemical property determined for each selected cutting of the same cluster to determine an average property value for the cluster.

Figure 10:
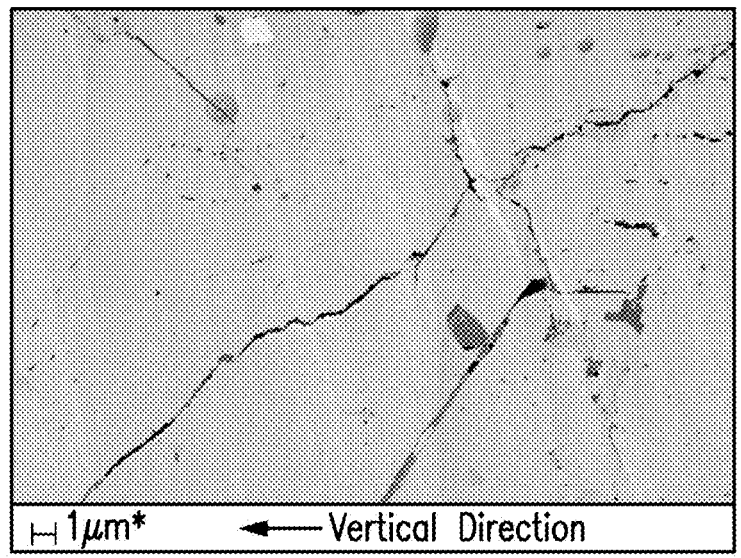
FIG. 10 is a SEM 2D image of sample B3 indicated in FIGS. 6-9 according to an example of the present invention.

For example, with respect to cutting selection and further analysis for property estimation, cuttings of two different clusters in the above example, particularly, cutting B3 of facies 2 and cutting D2 of facies 3, are identified and used herein for illustration. Other selected cuttings of the other clusters can be processed similarly as shown herein for cuttings B3 and D2. Before SEM scanning can be performed, the selected cuttings are removed from the carriers (step 612). For example, the selected cuttings can be exposed by laser cutting and pulled out. The isolated selected cuttings are scanned by SEM to produce 2D SEM images of the selected cuttings (step 613). The 2D SEM images that are produced for the indicated illustrative cuttings B3 and D2 are shown in FIGS. 10 and 11, respectively. FIG. 12 shows data points for about 20 SEM images taken at the same depth of the illustrative cuttings B3 and D2. FIGS. 13 and 14 show 3D voxel images obtained using a FIB-SEM for the subarea identified by the square in FIG. 11 (steps 614-615). FIG. 15 provides a chart of rock properties computed from the analysis of the indicated subarea of cutting D2. Other selected cuttings of the other clusters can be processed similarly as shown herein for cutting D2 to determine rock properties thereof. The equipment used for the 3D scans can be, for example, a Focused Ion Beam-Scanning Electron Microscope (FIB-SEM). The indicated method and system, or similar method and systems, can be used to segment the 3D image. Segmentation can be used at least in part to identify pores, grains, organic content, and porosity associated with organic content in the images (step 616). For example, once the segmented images have been produced, rock properties can be computed for each of the selected cuttings (step 617). As indicated, the determination of a rock property for a cutting can involve multiple different types of steps that can involve, for example, SEM scanning, FIB-SEM scanning, digital image processing and manipulations, and computations (e.g., calculations, estimations, and the like).

The computed rock property or properties for a selected cutting of each cluster can be considered representative of the other cuttings of the same cluster or family. Using the cluster occurrence frequency distribution, a statistical upscaling of the rock properties can be performed (step 618), for example, a weighted mean property value for a depth interval can be calculated using the following equation:

$$(\Sigma_{i=1}^{n} F_i P_i)/m$$

wherein i is the cluster number, n is the total number of clusters, F is the number of cuttings within the cluster i, P is the property value of the representative cutting for cluster i, and m is the total number of cuttings of all clusters.

Hypothetical Example of Mean Property Value Calculation for a Depth Interval

A non-limiting hypothetical example of the application of this equation to calculate mean porosity (e.g., average porosity) for a depth interval from which cuttings are obtained is provided as follows, with reference being made to the data pairs shown for Facies 1, 2, 3, and 4 in FIG. 9.

Facies 1: 3 cuttings=$F_1$
Facies 2: 6 cuttings=$F_2$
Facies 3: 11 cuttings=$F_3$
Facies 4: 2 cuttings=$F_4$ One selected cutting per facies (cluster) is investigated for the same selected property, such as porosity in this illustration:

Facies 1 selected cutting porosity: =2%=0.02=$P_1$
Facies 2 selected cutting porosity: =1%=0.01=$P_2$
Facies 1 selected cutting porosity: =7%=0.07=$P_3$
Facies 1 selected cutting porosity: =3%=0.03=$P_4$.

Use of the above-indicated equation for calculating a mean porosity for the depth interval provides the following ratios:

Mean porosity=$(F_1 P_1+F_2 P_2+F_3 P_3+F_4 P_4)$/(Total Number of Cuttings)

Mean Porosity=$[(3\times 0.02)+(6\times 0.01)+(11\times 0.07)+(2\times 0.03)]/22$ Mean Porosity=$(0.06+0.06+0.77+0.06)/22=0.95/22=0.04318$ (or 4.318%).

As illustrated, a mean porosity of 4.318% was calculated for the depth interval using the indicated equation. A similar calculation scheme can be applied to estimate other mean properties for a depth interval, such as total organic content, density, and the like.

Other methods of statistical upscaling of the rock properties can also be utilized. From the indicated determined frequency distributions of property values within a depth interval, various statistical measures can be computed. For example, if clusters based on such analysis can be classified as "pay" or "non-pay," then the sum of pay clusters' frequency becomes a measure of net-to-gross ratio. Another example can be obtaining porosity (e.g., average porosity), total organic content (TOC), density, and/or porosity associated with TOC values, within an individual cutting, such as illustrated above. After performing this analysis for a representative cutting selected from each cluster identified in a given depth interval, and combining the values with cuttings frequency distribution, the frequency distributions (histograms) of these values can be obtained within the depth range or interval. The mean porosity of the depth range, its mean TOC, and so forth, can be calculated. Porosity associated with TOC can be an indication of the maturity of the rock from which the cuttings are obtained, and can be used as a formation or facies assessment criterion. Clusters can be classified, such as those with high porosity and/or high TOC, according to one or more selected criterion value(s), as "pay," and other clusters not meeting the criterion value(s) can be classified as "non-pay," and the depth interval's net-to-gross ratio can be calculated as the sum of the frequencies of the pay clusters (step 619). As indicated, the analysis of steps 601-618 or 601-619 can be repeated for different depth intervals along the well, such as through all of the depth intervals thereof or a range of different intervals (step 622). A log can be provided that displays the frequency distribution of facies along the well, such as the entire well or other ranges of intervals of the well (step 623).

Figure 17:
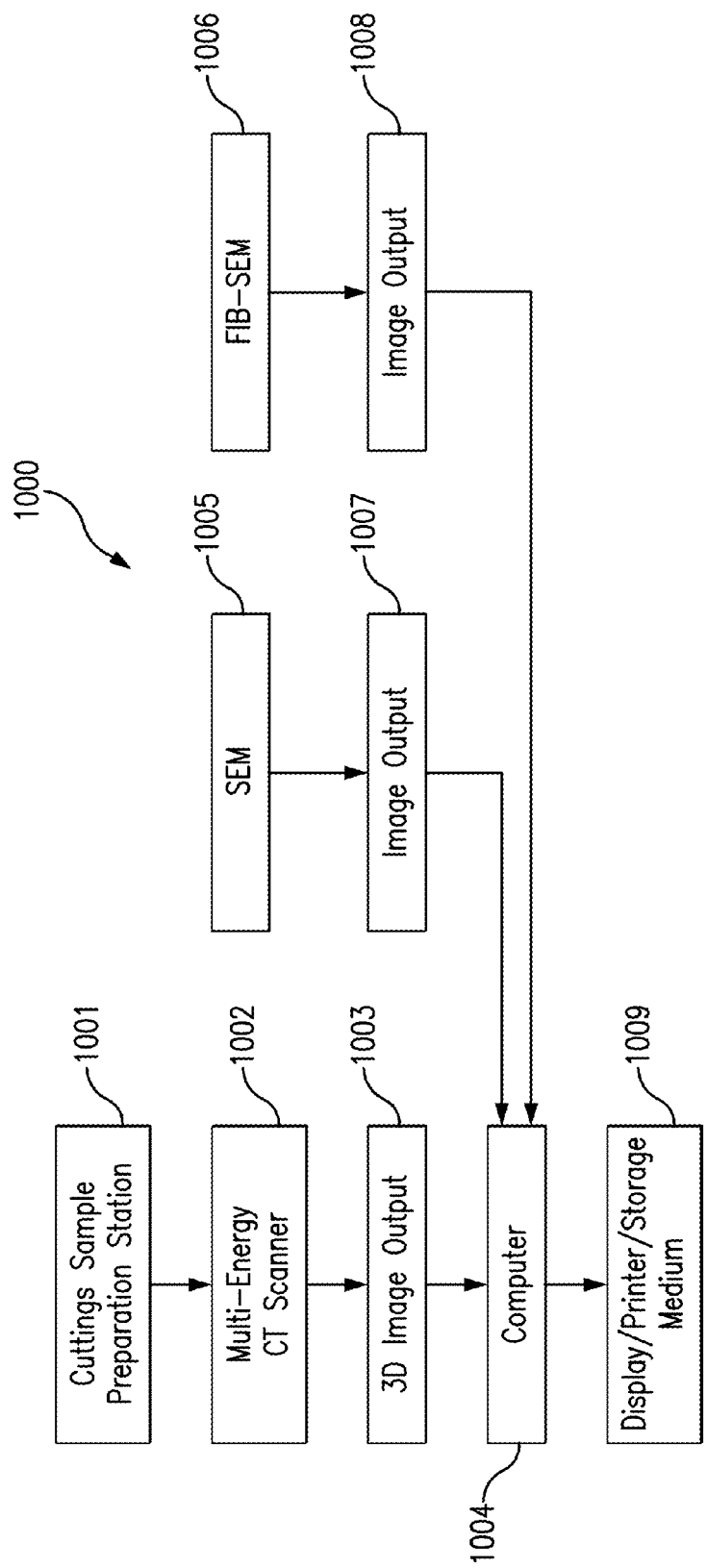
FIG. 17 is a system according to an example of the present application.

The present invention further comprises a system for implementing one or more of the methods as described above. As illustrated in FIG. 17, for example, the system 1000 can include a cuttings sample preparation station 1001 for preparing cuttings-embedded carriers as described herein. Three dimensional (3D) images of the cuttings embedded in a carrier or stacked carriers are generated by a multi-energy CT scanner 1002. The 3D image output 1003 of the scanner 1002 can be transferred to a computer 1004 having program instructions for carrying out the indicated 3D image analysis to organize the cuttings into categories based on data pairs of bulk density and effective atomic number and select a cutting or cuttings therefrom for further detailed analysis using a SEM 1005 and FIB-SEM 1006, which generate respective image outputs 1007 and 1008, which is analyzed in computer 1004 or other computer to perform the indicated data and simulation analysis to generate sample modeling output/results which can transmitted to one or more devices 1009, such as a display, a printer, data storage medium, or any combinations of these.

The system further can comprise one or more computer systems for processing images and computing rock properties. For example, the system can comprise one or more computer systems which can comprise software to capture images, process images, segment images, estimate rock properties, and any combinations thereof. The image processing can be done, for example, with data visualization and analysis software adapted for use in the present methods. The data visualization and analysis software can be used to process the images to do calculations for cropping the image matrix. After cropping the matrix, the image can be segmented. The data visualization and analysis software uses various image-processing techniques that include (a) noise reduction; (b) identifying the boundaries of the grains based on 3D surface gradients of the gray scale encountered in the original image; and (c) thresholding based on this image enhancement and focus sharpening. Other segmentation techniques can also be used, such as those described for example in U.S. Pat. No. 6,516,080 (Nur) and U.S. Patent Application Publication No. 2009/0288880 (Wojcik, et al), which are incorporated herein in their entireties by reference. The segmentation method described in the above incorporated U.S. Provisional Application No. 61/547,090 (Carpio, et al), published as U.S. Patent Application Publication No. 2013/0094716 A1, also can be used.

The system of the present invention can be located and used off-site or on-site with respect to where the samples are obtained. If used off-site, samples can be transported to the location where the system is located. If used on-site, the system optionally can be used in a mobile enclosure such as a trailer, van, motor coach or similar device; such that it can be transported to a well site and analyses run on-site.

It is to be understood that the methods described herein may be implemented in various forms of hardware, software, firmware, special purpose processors, or any combination thereof. For example, the 3D image output of the X-ray multi-energy scanner and 2D image output of a SEM and/or FIB-SEM can be transferred to a respective computer having program instructions for carrying out the applicable 3D or 2D image analysis described herein to generate output/results which can transmitted to one or more devices, such as a display device, a printer, data storage medium, or any combinations of these. The computer programs used for 3D image analysis and the computations can be stored, as a program product, on at least one computer usable storage medium (e.g. a hard disk, a flash memory device, a compact disc, a magnetic tape/disk, or other media) associated with at least one processor (e.g., a CPU) which is adapted to run the programs, or may be stored on an external computer usable storage medium which is accessible to the computer processor. The computer may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of a system including the scanner, computer, and output display and/or external data storage, can be connected to each other for communications (e.g., data transfer, etc.), via any of hardwire, radio frequency communications, telecommunications, internet connection, or other communication means.

The present invention also includes the following aspects/embodiments/features in any order and/or in any combination:

1. The present invention relates to a method for processing rock fragments for computer tomographic scanning, comprising positioning a plurality of rock fragments in space positions in a stabilizing material to provide a rock fragments-embedded carrier, and performing a multi-energy X-ray CT scan of the rock fragments-embedded carrier comprising the plurality of rock fragments with at least 3 reference objects.

2. The method of any preceding or following embodiment/feature/aspect, wherein the stabilizing material is a hardenable polymer, bone, putty, or foam.

3. The method of any preceding or following embodiment/feature/aspect, wherein the rock fragments are drill cuttings, micro-cores, crushed or broken core pieces, sidewall cores, or outcrop quarrying.

4. The present invention also relates to a method for preparing rock fragments for computer tomographic scanning which comprises steps of
(a) positioning a plurality of rock fragments retained in spaced positions in a casting container,
(b) introducing flowable polymer into the castings container to encapsulate the rock fragments,
(c) hardening the polymer to form a rock fragments-embedded carrier, and
(d) removing the rock fragments-embedded carrier from the casting container.

5. The method of any preceding or following embodiment/feature/aspect, wherein the positioning of step (a) further comprises retentively fitting the rock fragments into a mesh, and step (b) comprises introducing the flowable polymer into the casting container to encapsulate the rock fragments and the mesh.

6. The present invention also relates to a method for categorizing rock fragments within an X-ray digital scan for selection of a rock fragment for further digital analysis which comprises steps
(a) performing a multi-energy X-ray CT scan of a first rock fragments-embedded carrier comprising a first plurality of rock fragments,
(b) creating digital images of the rock fragments from the multi-energy X-ray CT scan, wherein each of the first plurality of rock fragments scanned at two or more different energy levels returns a CT value for each voxel thereof,
(c) estimating bulk density, RhoB, and effective atomic number, $Z_{eff}$, for each of the first plurality of rock fragments as data pairs based on the digital images of the rock fragments, comprising averaging the voxels for each entire rock fragment per different energy scan and processing the average values for each rock fragment to provide the data pairs,
(d) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (a), and
(e) selecting at least one rock fragment from the set or subsets as applicable for further digital analysis.

7. The method of any preceding or following embodiment/feature/aspect, wherein the first plurality of rock fragments are obtained from a same first interval.

8. The method of any preceding or following embodiment/feature/aspect, wherein the rock fragments-embedded carrier further comprising a second plurality of rock fragments obtained from a same second interval, wherein the first and second intervals are different.

9. The method of any preceding or following embodiment/feature/aspect, wherein the performing of the multi-energy X-ray CT scan of the step (a) further comprises scanning a second rock fragments-embedded carrier stacked with the first rock fragments-embedded carrier, wherein the second rock fragments-embedded carrier comprising a second plurality of rock fragments obtained from a second interval which is different than the first interval, and the steps (b), (c) and (d) are also done for the second rock fragments-embedded carrier.

10. The present invention also relates to a method for organizing and categorizing rock fragments within an X-ray digital scan for selection of a rock fragment for further digital analysis which comprises steps of:
(a) positioning a plurality of rock fragments in space positions in a stabilizing material to provide a rock fragments-embedded carrier,
(b) performing a multi-energy X-ray CT scan of the rock fragments-embedded carrier comprising the rock fragments with at least 3 reference objects,
(c) creating digital images of the rock fragments from the multi-energy X-ray CT scan, wherein each of the rock fragments scanned at two or more different energy levels returns a CT value for each voxel thereof,
(d) estimating the bulk density, RhoB, and effective atomic number, $Z_{eff}$, for each of the rock fragments as data pairs based on the digital images of the rock fragments, comprising averaging the voxels for the entire rock fragment per different energy scan and processing the average values for each rock fragment to provide the data pairs, (e) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (e), and (f) selecting at least one rock fragment from the set or subsets as applicable for further digital analysis.

11. The present invention also relates to a method for organizing and categorizing rock fragments within an X-ray digital scan for selection of a rock fragment for further digital, analysis which comprises steps of:

(a) positioning rock fragments of the same drilling interval in spaced positions in a casting container, (b) introducing flowable polymer into the casting container to encapsulate the rock fragments, (c) hardening the polymer to form a rock fragments-embedded carrier, (d) removing the rock fragments-embedded carrier from the casting container, (e) performing a multi-energy X-ray CT scan of the rock fragments-embedded carrier comprising the rock fragments with at least 3 reference objects, (f) creating digital images of the rock fragments from the multi-energy X-ray CT scan, (g) estimating the bulk density, RhoB, and effective atomic number, $Z_{eff}$, for each of the rock fragments as data pairs based on the digital images of the rock fragments as indicated, (h) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (e), and (i) selecting at least one rock fragment from the set or subsets as applicable for further digital analysis.

12. The method of any preceding or following embodiment/feature/aspect, wherein the rock fragments comprise rock fragments having a maximum diameter of from about 0.5 mm to about 5 mm.

13. The method of any preceding or following embodiment/feature/aspect, wherein the rock fragments have an aspect ratio from 0.2 to 1.

14. The method of any preceding or following embodiment/feature/aspect, wherein the rock fragments comprise shale rock fragments.

15. The method of any preceding or following embodiment/feature/aspect, wherein the positioning comprises retentively fitting the rock fragments into a mesh.

16. The method of any preceding or following embodiment/feature/aspect, wherein the polymer comprises curable epoxy.

17. The method of any preceding or following embodiment/feature/aspect, wherein the multi-energy X-ray CT scan comprising a dual energy X-ray CT scan.

18. The method of any preceding or following embodiment/feature/aspect, further comprising:

(i) repeating steps (a)-(d) for rock fragments from a plurality of different drilling intervals before step (e) to provide a plurality of rock fragments-embedded carriers, (ii) stacking the plurality of rock fragments-embedded carriers in a scanning stage of a multi-energy X-ray CT scanner, and optionally surrounding the scanner stage by an x-ray attenuating sleeve, (iii) performing a multi-energy X-ray CT scan of the stack of rock fragments-embedded carriers, (iv) performing steps (f)-(i) for at least two of the rock fragments-embedded carriers.

19. The method of any preceding or following embodiment/feature/aspect, wherein the casting container has a cylindrical shape.

20. The method of any preceding or following embodiment/feature/aspect, wherein about 10 to about 15 rock fragments are positioned in the casting container in step (a).

21. The method of any preceding or following embodiment/feature/aspect, wherein the rock fragments-embedded carrier is disc shaped.

22. The method of any preceding or following embodiment/feature/aspect, wherein the rock fragments-embedded carrier is disc shaped and having a thickness of from about 2 mm to about 5 mm.

23. The method of any preceding or following embodiment/feature/aspect, wherein the performing of the multi-energy X-ray CT scan of the rock fragments-embedded carrier is performed in the presence of at least three calibration materials.

24. The present invention also relates to a method for estimating selected physical properties of a rock sample, which comprises the steps of:

(a) positioning rock fragments of the same drilling interval in spaced positions in a casting container, (b) introducing flowable polymer into the casting container to encapsulate the rock fragments, (c) hardening the polymer to form a rock fragments-embedded carrier, (d) removing the rock fragments-embedded carrier from the casting container, (e) performing a multi-energy X-ray CT scan of the rock fragments-embedded carrier with at least 3 reference objects, (f) creating digital images of the rock fragments from the multi-energy X-ray CT scan, (g) estimating the bulk density, RhoB, and effective atomic number, $Z_{eff}$, for the rock fragments as data pairs based on the digital images of the rock fragments as indicated, (h) categorizing the bulk density, RhoB, and effective atomic number, $Z_{eff}$, data pairs into a single set for a single rock fragments-embedded carrier or separate subsets if more than one rock fragments-embedded carrier of differing intervals is scanned in step (e), (i) selecting at least one rock fragment from the set or subsets as applicable for further digital analysis, (j) extracting the at least one selected rock fragment from the carrier, (k) creating 2D digital images of the selected rock fragment using an SEM, (l) estimating at least one of porosity, organic matter content, and mineralogy from the images created in step (k), (m) selecting a subarea of the images created in step (k), which can comprise at least one of relatively high porosity and high organic matter or other features of interest, (n) imaging the selected subarea of step (m) with a FIB-SEM, (o) creating 3D digital images from the imaging in step (n), (p) segmenting the 3D digital images of step (o) to identify voxels as pore, rock or organic matter, and (q) estimating rock properties from the segmented images.

25. The method of any preceding or following embodiment/feature/aspect, wherein the positioning of the rock fragments in step (a) comprises positioning the rock fragments in spaced apart locations of a polymeric mesh having a circular shape which fits within an inner opening defined by the casting container.

26. The method of any preceding or following embodiment/feature/aspect, wherein the polymer comprises curable epoxy.

27. The method of any preceding or following embodiment/feature/aspect, further comprising:
(i) repeating steps (a)-(d) for rock fragments from a plurality of different drilling intervals before step (e) to provide a plurality of rock fragments-embedded carriers,
(ii) stacking the plurality of rock fragments-embedded carriers in a scanning stage of a multi-energy X-ray CT scanner,
(iii) performing a multi-energy X-ray CT scan of the stack of rock fragments-embedded carriers,
(iv) performing steps (f)-(q) for at least two of the rock fragments-embedded carriers.

28. The present invention relates to a method for characterizing facies occurrence frequency of a depth interval using rock fragments, comprising:
(a) performing a multi-energy X-ray CT scan of a plurality of rock fragments of a depth interval with at least 3 reference objects at two or more different energy levels;
(b) creating digital images of the rock fragments from the multi-energy X-ray CT scan, wherein each of the rock fragments scanned at two or more different energy levels returns for each energy a CT value for each voxel thereof;
(c) estimating bulk density, RhoB, and effective atomic number, $Z_{\mathit{eff}}$, for each of the rock fragments as data pairs based on the digital images of the rock fragments, comprising averaging the voxels for each entire rock fragment per different energy scan and processing the average values for each rock fragment to provide the data pairs;
(d) categorizing the bulk density, RhoB, and effective atomic number, $Z_{\mathit{eff}}$, data pairs and identifying clusters, wherein the clusters identify different respective facies of rock of the depth interval; and
(e) determining an occurrence frequency distribution of the rock fragments with respect to the clusters based on the number of rock fragments in each cluster and the total number of rock fragments, wherein the occurrence frequency distribution of the rock fragments correlates with occurrence frequency distribution of the identified facies in the depth interval.

29. The method of any preceding or following embodiment/feature/aspect, further comprising the steps of:
(i) repeating steps (a)-(e) for a plurality of additional different depth intervals along an entire well; and
(ii) forming a log that displays frequency distributions of facies for a plurality or all of the different depth intervals along the well.

30. The method of any preceding or following embodiment/feature/aspect, wherein the categorizing of the bulk density, RhoB, and effective atomic number, $Z_{\mathit{eff}}$, data pairs into clusters, comprises grouping data pairs that have similar bulk density, RhoB, and effective atomic number, $Z_{\mathit{eff}}$, into respective clusters.

31. The method of any preceding or following embodiment/feature/aspect, further comprising the steps:
(f) selecting a rock fragment from each cluster;
(g) determining a rock property value for a same rock property for a representative rock fragment selected from each cluster to provide respective determined rock property values; and
(h) calculating a weighted mean value for the rock property for the depth interval based on the determined rock property values and the occurrence frequency of the clusters.

32. The method of any preceding or following embodiment/feature/aspect, further comprising the steps:
(f) selecting a rock fragment from each cluster;
(g) determining a rock property value for a same rock property for the rock fragment selected for each cluster to provide determined rock property values; and
(h) determining a frequency distribution of property values within the depth interval.

33. The method of any preceding or following embodiment/feature/aspect, wherein the same rock property is total porosity, total organic content, porosity associated with total organic content, or permeability.

34. The method of any preceding or following embodiment/feature/aspect, further comprising classifying the clusters having (i) a value of porosity meeting a predetermined criterion, (ii) a value of total organic content meeting a predetermined criterion, or (iii) both, as pay, and calculating a net-to-gross ratio for the depth interval as a sum of the frequencies of the pay clusters.

35. The method of any preceding or following embodiment/feature/aspect, further comprising, prior to step (a),
(i) positioning at least a portion of the plurality of the rock fragments of a depth interval in spaced apart locations within an inner opening defined by a casting container,
(ii) introducing flowable polymer into the casting container to encapsulate the rock fragments,
(iii) hardening the polymer to form an X-ray CT scannable rock fragments-embedded carrier,
(iv) removing the X-ray CT scannable rock fragments-embedded carrier from the casting container, and
(v) for any remaining rock fragments of the plurality of rock fragments not included in the portion of the plurality of the rock fragments of step (i), repeating steps (i)-(iv) one or more times until all the plurality of rock fragments are provided in an X-ray CT scannable rock fragments-embedded carrier.

36. The present invention also relates to a method for determining a bulk property of a depth interval of a rock formation, comprising:
(a) obtaining a sample of a depth interval of a rock formation, the sample comprising a plurality of rock fragments;
(b) imaging the plurality of rock fragments from the depth interval with at least 3 reference objects using dual energy X-ray CT scanning;
(c) estimating bulk density, RhoB, and effective atomic number, $Z_{\mathit{eff}}$, for each of the rock fragments as data pairs based on the digital images of the rock fragments, which comprises averaging the voxels for each entire rock fragment per different energy scan and processing the average values for each rock fragment to provide the data pairs;
(d) categorizing the bulk density, RhoB, and effective atomic number, $Z_{\mathit{eff}}$, data pairs and identifying clusters, wherein the clusters identify different respective facies of rock of the depth interval;
(e) determining a physical or chemical property of at least one rock fragment of each of the different facies, the physical or chemical property determined being the same for each rock fragment of the different facies of the at least one rock fragment;
(f) calculating the frequency distribution of each of the different facies based on the total number of rock fragments in the plurality of rock fragments and the total number of rock fragments of each of the different facies of the plurality of different facies; and
(g) determining a bulk property of the depth interval based on the determined physical or chemical property of the rock fragments of the different facies and the frequency distribution of each of the different facies.

37. The method of any preceding or following embodiment/feature/aspect, wherein the rock formation comprises a subterranean rock formation.

38. The method of any preceding or following embodiment/feature/aspect, wherein the bulk property comprises one of bulk density, average porosity, average total organic content, average porosity associated with total organic content.

39. The method of any preceding or following embodiment/feature/aspect, wherein the step (e) comprises determining the physical or chemical property of a plurality of rock fragments of each of the different facies and averaging a value of the physical or chemical property to determine an average property for each of the different facies.

40. The method of any preceding or following embodiment/feature/aspect, further comprising obtaining a sample of a different depth interval of the rock formation and determining a bulk property of the different depth interval.

41. The method of any preceding or following embodiment/feature/aspect, further comprising comparing the bulk property determined at the depth interval to a bulk property previously determined for the same depth interval of a neighboring rock formation and verifying the bulk property determined if it is about the same as the bulk property previously determined for the neighboring rock formation.

42. The present invention also relates to a system for organizing and categorizing rock fragments within an X-ray digital scan for selection of a rock fragment for further analysis, comprising:
(a) a preparation station comprising a plurality of rock fragments of a same drilling interval positioned in spaced apart locations of a polymeric mesh having a shape finable within an inner opening defined by a casting container, wherein the rock fragments are embedded in a hardened polymer to provide a rock fragments-embedded carrier,
(b) a multi-energy X-ray CT scanner having a stage capable of holding one or more rock fragments-embedded carriers in stacked arrangement and a plurality of reference objects during scanning thereof, and optionally including an attenuating sleeve surrounding the scanner stage, and
(c) one or more computer systems operable to estimate the bulk density, RhoB, and effective atomic number, $Z_{eff}$, as data pairs for layers of voxels (slices) in digital images obtained from scanning the rock fragments as indicated, and output the results to at least one device to display, print, or store results of the computations.

43. The present invention also relates to a system for characterizing facies occurrence frequency of a depth interval using rock fragments, comprising:
(a) a preparation station comprising a plurality of rock fragments of the same depth interval positioned in spaced apart locations within an inner opening defined by a casting container, wherein the rock fragments are embedded in a hardened polymer to provide a rock fragments-embedded carrier,
(b) a multi-energy X-ray CT scanner having a stage capable of holding one or more rock fragments-embedded carriers retaining the plurality of rock fragments in stacked arrangement and a plurality of reference objects during scanning thereof, and optionally including an attenuating sleeve surrounding the scanner stage, and
(c) one or more computer systems operable to (i) estimate bulk density, RhoB, and effective atomic number, $Z_{eff}$, for each of the rock fragments as data pairs based on the digital images of the rock fragments, comprising averaging the voxels for each entire rock fragment per different energy scan and processing the average values for each rock fragment to provide the data pairs, (ii) plot the bulk density, RhoB, and effective atomic number, $Z_{eff}$, data pairs for categorization and identification of clusters, wherein the categorized clusters identify different respective facies of rock of the depth interval, (iii) determine an occurrence frequency distribution of the rock fragments with respect to the clusters based on the number of rock fragments in each cluster and the total number of rock fragments, wherein the occurrence frequency distribution of the rock fragments correlate with occurrence frequency distribution of the identified facies in the depth interval, and (iv) output the results to at least one device to display, print, or store results of the computations.

44. The present invention also relates to a computer program product on a computer readable medium that, when performed on a processor in a computerized device provides a method for performing computations of one or more or all of the indicated steps of any of the methods described herein.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:
1. A method for estimating selected physical properties of a rock sample, which comprises the steps of:
   (a) positioning rock fragments of the same drilling interval in spaced positions in a casting container,
   (b) introducing flowable polymer into the casting container to encapsulate the rock fragments,
   (c) hardening the polymer to form a rock fragments-embedded carrier,
   (d) removing the rock fragments-embedded carrier from the casting container,
   (e) performing a multi-energy X-ray CT scan of the rock fragments-embedded carrier with at least 3 reference objects,
   (f) creating digital images of the rock fragments from the multi-energy X-ray CT scan, wherein each of the rock fragments scanned at two or more different energy levels returns a CT value for each voxel thereof,
   (g) estimating the bulk density, RhoB, and effective atomic number, $Z_{eff}$, for each of the rock fragments as data pairs based on the digital images of the rock fragments, comprising averaging the voxels for each entire rock fragment per different energy scan and processing the average values for each rock fragment to provide the data pairs, (h) categorizing the bulk density, RhoB, and effective atomic number, $Z_{\mathit{eff}}$, data pairs into a single set for a single rock fragments-embedded carrier or separate subsets if more than one rock fragments-embedded carrier of differing intervals is scanned in step (e), (i) selecting at least one rock fragment from the set or subsets as applicable for further digital analysis, (j) extracting the at least one selected rock fragment from the carrier, (k) creating 2D digital images of the selected rock fragment using an SEM, (l) estimating at least one of porosity, organic matter content, and mineralogy from the images created in step (k), (m) selecting a subarea of the images created in step (k), which can comprise at least one of relatively high porosity and high organic matter or other features of interest, (n) imaging the selected subarea of step (m) with a FIB-SEM, (o) creating 3D digital images from the imaging in step (n), (p) segmenting the 3D digital images of step (o) to identify voxels as pore, rock or organic matter, and (q) estimating rock properties from the segmented images.

2. The method of claim 1, wherein the positioning of the rock fragments in step (a) comprises positioning the rock fragments in spaced apart locations of a polymeric mesh having a circular shape which fits within an inner opening defined by the casting container.

3. The method of claim 1, wherein the polymer comprises curable epoxy.

4. The method of claim 1, further comprising:
(i) repeating steps (a)-(d) for rock fragments from a plurality of different drilling intervals before step (e) to provide a plurality of rock fragments-embedded carriers,
(ii) stacking the plurality of rock fragments-embedded carriers in a scanning stage of a multi-energy X-ray CT scanner,
(iii) performing a multi-energy X-ray CT scan of the stack of rock fragments-embedded carriers,
(iv) performing steps (f)-(q) for at least two of the rock fragments-embedded carriers.

* * * * *